United States Patent [19]

Godec et al.

[11] Patent Number: 5,443,991

[45] Date of Patent: Aug. 22, 1995

[54] METHOD FOR THE DETERMINATION OF DISSOLVED CARBON IN WATER

[75] Inventors: Richard D. Godec, Erie; Paul K. Kosenka, Estes Park; Richard Hutte, Boulder, all of Colo.

[73] Assignee: Sievers Instruments, Inc., Boulder, Colo.

[21] Appl. No.: 869,308

[22] Filed: Apr. 16, 1992

Related U.S. Application Data

[62] Division of Ser. No. 487,720, Mar. 2, 1990, Pat. No. 5,132,094.

[51] Int. Cl.$^6$ ............................................. G01N 33/00
[52] U.S. Cl. ........................................ 436/145; 436/147
[58] Field of Search ................. 436/145, 146; 204/129; 210/746, 96.1

[56] References Cited

U.S. PATENT DOCUMENTS

| | | | |
|---|---|---|---|
| 3,224,837 | 12/1965 | Moyat | 204/153.1 |
| 3,459,938 | 8/1969 | Stenger et al. | 436/146 |
| 3,607,071 | 9/1971 | Staffin et al. | 436/146 |
| 3,854,881 | 12/1974 | Cohen | 436/146 |
| 3,958,941 | 5/1976 | Regan | 422/80 |
| 4,209,299 | 6/1980 | Carlson | 204/153.2 |
| 4,277,438 | 7/1981 | Ejzak | 436/146 |
| 4,288,229 | 9/1981 | Mar | 436/146 |
| 4,293,522 | 10/1981 | Winkler | 204/153.2 |
| 4,504,373 | 3/1985 | Mani et al. | 204/182.4 |
| 4,529,495 | 7/1985 | Marsoner | 422/82.03 |
| 4,619,902 | 10/1986 | Bernard | 422/78 |
| 4,626,413 | 12/1986 | Blades et al. | 422/78 |
| 4,666,860 | 5/1987 | Blades et al. | 436/146 |
| 4,775,634 | 10/1988 | Sienkiewicz | 210/758 |

*Primary Examiner*—W. Gary Jones
*Assistant Examiner*—Laura E. Edwards
*Attorney, Agent, or Firm*—Beaton & Folsom

[57] ABSTRACT

Apparatus and methods for the measurement of total organic carbon and total inorganic and organic content of water are described. A novel combination of an acidification module, and inorganic carbon removal module based on a carbon dioxide selective gas permeable membrane, and oxidation reaction system which incorporates in-situ generation of oxidizing agents, coupled with catalyzed photo-oxidation of organic compounds to form carbon dioxide, and a high sensitivity, conductometric detector employing a carbon dioxide selective gas permeable membrane permits on-line measurement of the total organic carbon content of water streams.

11 Claims, 15 Drawing Sheets

178

METHOD FOR THE DETERMINATION OF DISSOLVED CARBON IN WATER

This is a divisional application of Ser. No. 07/487,720, filed Mar. 2, 1990, now U.S. Pat. No. 5,132,094.

FIELD OF THE INVENTION

The present invention relates to an improved method and apparatus for the determination of the total concentration of organic and/or inorganic carbon compounds in aqueous process streams and in bulk solutions. Particularly, the method of the present invention includes the acidification of an aqueous sample stream, the in-situ generation of oxidizing agents—including oxygen, hydrogen peroxide and peroxydisulfate or persulfate ion—used in conjunction with semiconductor-catalyzed photo-oxidation of organic compounds to form carbon dioxide, and the sensitive and selective detection of carbon dioxide utilizing a gas permeable membrane and conductometric detection.

BACKGROUND OF THE INVENTION

The measurement of the total organic carbon (TOC) concentration and total carbon concentration in water has become a standard method for accessing the level of contamination of organic compounds in potable waters, industrial process waters, and municipal and industrial waste waters. In addition to widespread terrestrial applications, the measurement of TOC is one of the primary means of determining the purity of potable and process waters for manned space based systems including the space shuttle, the proposed space station and for future manned explorations of the moon and other planets.

A variety of numerous prior art approaches for measuring the total organic carbon content of water have been proposed. For example, See U.S. Pat. No. 3,958,941 of Regan; U.S. Pat. No. 3,224,837 of Moyat; U.S. Pat. No. 4,293,522 of Winkler; U.S. Pat. No. 4,277,438 of Ejzak; U.S. Pat. Nos. 4,626,413 and 4,666,860 of Blades et. al.; and U.S. Pat. No. 4,619,902 of Bernard.

Representative of the devices described in these references are the methods disclosed in U.S. Pat. No. 3,958,941 of Regan. In Regan an aqueous sample is introduced into a circulating water stream that flows through a reaction chamber where the sample is mixed with air and exposed to ultraviolet (U.V.) radiation to promote the oxidation of organic compounds to form carbon dioxide. The carbon dioxide formed in the reaction chamber is then removed from solution by an air stripping system and introduced into a second chamber containing water that has been purified to remove ionic compounds. The conductivity of the water in the second chamber is measured, and any increase in conductivity is related to the concentration of carbon dioxide formed in the first reactor. The conduction measurement can be used, therefore, to determine the concentration of organic compounds in the original sample.

The Regan device is slow, cannot be used for the continuous monitoring of TOC concentration in aqueous streams, cannot be scaled down without increasing interference from $NO_2$, $CO_2$ and $H_2S$ to unacceptable levels, and is generally unsatisfactory. In addition, Regan does not disclose that an aqueous solution of acid must be added to the sample stream to reduce the pH to a value of less than about 4 to insure reasonable removal rate of carbon dioxide using the air stripping system described. The oxidation method disclosed by Regan is unsatisfactory for the measurement of refractory compounds, particularly urea. In Regan, an aqueous sample of 20 to 100 mL containing 0.5 mg/L organic carbon is required to generate sufficient carbon dioxide for accurate detection, thus limiting the utility of the device for the measurement of sub-part per million levels of TOC in smaller sample sizes. Finally, in practice, the Regan system requires frequent recalibration—typically once per day—due to variations in background conductivity. Also, the concentration of total organic carbon in the calibration standard must be approximately equal to the concentration of organic carbon in the sample. Because of this, recalibration is required when analyzing aqueous samples containing higher or lower levels of organic carbon when compared with the calibration standard.

An improved method and apparatus for the measurement of organic content of aqueous samples is that disclosed in U.S. Pat. No. 4,277,438 of Ejzak. Ejzak describes a multistage reactor design which provides for the addition of oxygen and a chemical oxidizing agent, preferably sodium persulfate, to the aqueous sample stream prior to oxidation of the stream using ultraviolet radiation in a series of reactors. Ejzak also describes the use of an inorganic carbon stripping process—before oxidation of the organic carbon—that includes the addition of phosphoric acid to the sample stream. After oxidation, the sample stream is passed into a gas-liquid separator where the added oxygen acts as a carrier gas to strip carbon dioxide and other gases from the aqueous solution. In the preferred embodiment, the gas stream is then passed through an acid mist eliminator, a coalescer and salt collector, and through a particle filter prior to passage into an infrared (IR) detector for the measurement of the concentration of carbon dioxide in the gas stream.

The methods and apparatus disclosed by Ejzak provide improvements over the teachings of Regan, however, the Ejzak device requires extensive manual operation and is also generally unsatisfactory. The Ejzak device requires three external chemical reagents; oxygen gas, aqueous phosphoric acid and an aqueous solution of sodium persulfate. Both the phosphoric acid and persulfate solutions must be prepared at frequent intervals by the operator due to the relatively high rate of consumption. The Ejzak device requires dilution of the sample if the solution contains high concentrations of salts in order to insure complete oxidation of the sample and to eliminate fouling of the particle filter located prior to the IR carbon dioxide detector. As with Regan, relatively large sample sizes are required—typically 20 mL of sample for accurate measurement at 0.5 mg/L total organic carbon—and the carbon dioxide formed in the oxidation chamber is removed using a gravity dependent technique that cannot be easily used in space-based operations.

Another improved method and apparatus for the measurement of total organic carbon in water is disclosed in U.S. Pat. No. 4,293,522 of Winkler. In Winkler, an oxidizing agent, molecular oxygen, is generated in-situ by the electrolysis of water. Organic compounds are subsequently oxidized to form carbon dioxide by the combination of U.V. radiation and the in-situ generated oxygen. The irradiation and electrolysis processes are both accomplished in a single oxidation chamber. Winkler does not teach that the aqueous sample stream be acidified to assist in the removal of carbon dioxide from solution, and in fact teaches against the use of acid. Therefore, this method and apparatus cannot be used for the measurement of organic compounds in basic aqueous samples. The oxidation chamber of Winkler uses a solid electrolyte to separate the two electrodes employed for the electrolysis of water. The solid electrolyte described by Winkler is composed of an organic polymer which, under exposure to oxygen, ozone and U.V. radiation, will undergo oxidation to form carbon dioxide; therefore, resulting in unacceptable background levels of organic compounds in the sample stream, particularly at low organic compound concentrations.

Winkler also describes a conductometric carbon dioxide detection system wherein the sample stream exiting the oxidizing chamber is held in an equilibrating relationship to a stream of deionized water. The two flowing streams are separated by a gas permeable membrane that allows the concentration of carbon dioxide to equilibrate between the streams. The concentration of the carbon dioxide is thereby determined by measuring the conductance of the deionized water stream. However, the use of two flowing streams introduces operating parameters into the detection process that require frequent calibration adjustments.

Another example of the prior art is that disclosed in U.S. Pat. No. 4,619,902 of Bernard, which teaches the oxidation of organic compounds to form carbon dioxide using persulfate oxidation at elevated temperatures—typically 20° to 100° C.—in the presence of a platinum metal catalyst. Bernard recognizes that the materials used in the construction of instrumentation for the determination of total organic carbon in water can contribute organic compounds to the sample during the measurement process, and teaches that inert materials such as PTFE must be used to reduce this background from the measurement. As with the previously mentioned disclosures, a gas stripping technique is employed to collect the formed carbon dioxide, and measurement is made using IR spectrometry. Bernard also recognizes that aqueous solutions of sodium persulfate are not stable due to auto-degradation of the reagent.

An improved system for the measurement of organic compounds in deionized water is disclosed in U.S. Pat. No. 4,626,413 of Blades and Godec. The apparatus described by Blades and Godec is based on direct U.V. oxidation of organic compounds to form carbon dioxide which is measured by using conductometric detection. In the apparatus described in Blades and Godec, the oxidation of some organic compounds from such strong acids such as HCl, $H_2SO_4$ and $HNO_3$ which interfere with the conductometric method. The Blade device is also limited to the measurement of total organic compounds in deionized water and cannot be used for samples containing ionic compounds other than bicarbonate ion.

In U.S. Pat. No. 4,209,299 of Carlson, it is disclosed that the concentration of volatile materials in a liquid can be quantitatively determined by transferring the desired material through a gas permeable membrane into a liquid of known conductivity, such as deionized water. The Carlson device is demonstrated for the measurement of a number of volatile organic and inorganic compounds, but Carlson does not suggest the combination of this process in conjunction with a carbon dioxide producing reactor.

The use of aqueous solutions of persulfate salts for the oxidation of organic compounds is widely known. Smit and Hoogland (16 Electrochima Acta, 1–18 (1971)) demonstrate that persulfate ions and other oxidizing agents can be electrochemically generated.

In U.S. Pat. No. 4,504,373 of Mani et. al., a method for the electrochemical generation of acid and base from aqueous salt solutions is disclosed.

In electrochemical reactions in aqueous solutions, a common reduction product is hydrogen gas. Because of its flammability, the hydrogen presents a potential hazard in devices using electrochemical techniques. The interaction of hydrogen gas in aqueous solutions and palladium metal is well known (e.g., F A. Lewis, "The Palladium Hydrogen System," Academic Press, 1967, London, incorporated herein by this reference) and the use of palladium offers a potential solution to the generation of hydrogen in electrochemical reactions by selective removal and disposal of the hydrogen.

SUMMARY OF THE INVENTION

Recognizing the need for accurate on-line measurement of the concentration of total organic and inorganic carbon compounds in aqueous streams and the problems and limitations of existing methods and apparatus used for these measurements, the present invention provides a novel method and apparatus which eliminates or overcomes these problems. Specifically, the present invention incorporates four significant advantages; 1) the carbon dioxide detector described herein utilizes a selective gas permeable membrane for the transport of carbon dioxide either from the oxidized or unoxidized sample stream into a second aqueous solution where the sensitive detection of carbon dioxide is accomplished using conductometric measurement, thus eliminating the use of a gas stripping apparatus, 2) in-situ generation of oxidizing agents including persulfate ions, hydrogen peroxide and molecular oxygen, thus eliminating the need for the introduction of gases and unstable chemical reagents, 3) an in-line acidification module which permits accurate determination of the organic content of aqueous samples over a wide sample pH range, and 4) the incorporation of an oxidation catalyst to insure rapid and complete photo-oxidation of organic compounds.

In one embodiment of the present invention, an aqueous sample stream is passed through a filter to remove any particulate matter, and passed into a acidification module for the introduction of a suitable concentration of acid to cause a reduction in the pH of the solution to a pH of less than 4. Inorganic carbon species—primarily carbonate and bicarbonate ions—are reacted with the acid to form carbon dioxide, while organic compounds remain unreacted.

The effluent of the acidification module is directed into an inorganic carbon removal module comprised of a carbon dioxide selective gas permeable membrane or a non-selective gas permeable membrane, which separates the acidified sample stream from a second aqueous stream in which the pH of the stream has been raised to a pH of greater than 10 by addition of a suitable base. The carbon dioxide formed from the reaction of inorganic carbon species with the acid will selectively diffuse across the gas permeable membrane into the basic aqueous stream where the carbon dioxide will be converted to ionic species (carbonate or bicarbonate) for subsequent disposal.

The acidic and basic streams used in the acidification module and inorganic carbon removal modules may be composed of aqueous solutions of suitable acids and bases or alternatively, an aqueous salt solution can be passed through a system incorporating a bi-polar membrane (see U.S. Pat. No. 4,504,373, specifically incorporated herein by this reference) for the in-situ generation of an acidic stream, a basic stream, and a depleted salt stream.

The effluent of the inorganic carbon removal module is then directed into a U.V. oxidation module which incorporates either direct U.V. oxidation using short wavelength U.V. radiation, semiconductor catalyzed U.V. oxidation using short wavelength U.V. radiation, or U.V. oxidation in the presence of oxygen and or other oxidizing agents such as persulfate, which are generated in-situ by the electrolysis of water and other chemical reagents such as sodium sulfate. In the U.V. oxidation reactor, organic compounds are converted to carbon dioxide. A palladium cathode system can be employed in the electrolysis apparatus for the removal of any hydrogen generated during the electrolysis of water.

The carbon dioxide formed in the photoreactor is then sensitively measured using a novel carbon dioxide sensor. The sensor is comprised of a carbon dioxide selective gas permeable membrane which separates the acidified sample stream from a deionized water reservoir. The deionized water is continuously generated by means of a mixed bed ion exchange resin. Alternatively, deionized water can be supplied from a source external to the apparatus described in the present invention.

In the basic measurement cycle, a fresh pulse of deionized water is introduced into the deionized water side of the gas permeable membrane and a shut-off valve actuated to stop the flow of deionized water. The effluent of the photoreactor continuously flows on the opposite side of the membrane. The carbon dioxide formed in the photoreactor from the oxidation of organic compounds diffuses across the gas permeable membrane until the concentration of carbon dioxide in the two aqueous streams is substantially the same. As the carbon dioxide enters the deionized water, the carbon dioxide will dissolve in the water and cause an increase in the conductivity of the aqueous solution. After equilibrium has been established (typically about 5 min.), a fresh pulse of deionized water is introduced to sweep the equilibrated solution into a conductivity cell in order to measure the increase in the concentration of ionic species.

The increase in conductivity observed in the deionized water can be directly related to the concentration of carbon dioxide in the sample stream and hence the level of organic compounds originally present in the sample stream.

In an alternate embodiment of the present invention, the apparatus can be modified to permit measurement of the total carbon content of the sample and the total inorganic carbon content of the sample. In this embodiment, the inorganic carbon removal module is replaced with two three-way valves which permit the acidified sample stream to bypass the photo-reactor. The concentration of total inorganic carbon in the aqueous sample is determined when the photoreactor is bypassed and the acidified sample stream proceeds directly into the sample side of the gas permeable membrane component of the carbon dioxide sensor. As described above, equilibration of the carbon dioxide present in the sample stream, due to the reaction of inorganic carbon species with a suitable acid, will cause an increase in the conductivity on the deionized water side of the sensor and this increased conductivity can be measured by using a conductivity cell and directly related to the concentration of inorganic carbon species present in the aqueous sample.

After measurement of the total inorganic carbon concentration, the two three-way valves are repositioned to allow the acidified aqueous stream to pass through the photoreactor for the oxidation of organic compounds to form carbon dioxide. In this operational mode, the carbon dioxide sensor component will determine the total carbon content of the sample stream (total inorganic and organic carbon concentrations). The level of organic compounds in the sample is then determined from the difference between the total carbon concentration and the previously measured total inorganic carbon concentration.

In a third embodiment of the present invention, the use of the stream splitter and three-way valve is replaced with a flow-through system which incorporates an external switch for the electrical connections to the U.V. photoreactor. Without a source of U.V. radiation, organic compounds in the acidified sample stream will not be converted to carbon dioxide, while inorganic carbon species will react with the added acid to form carbon dioxide, which is detected by the carbon dioxide sensor. After the measurement of total inorganic carbon, the electrical power to the source of ultraviolet radiation is restored, resulting in the coversion of organic compounds to carbon dioxide. After irradiation, the level of carbon dioxide in the sample stream, as measured by the carbon dioxide sensor, will be proportional to the level of total carbon species (organic and inorganic) present in the sample. The level of total organic carbon in the sample stream is then computed from the difference between the detector response with the U.V. lamp on (total carbon) and the lamp off (total inorganic carbon).

DETAILED DESCRIPTION OF THE PREFERRED EMBODIMENT

The measurement of the total organic content of aqueous samples has become a standard technique for determining the quality of potable water, industrial process water and industrial and municipal waste waters.

The determination of the organic content of water samples is most commonly achieved by oxidation of the organic constituents to carbon dioxide using chemical oxidizing agents, U.V. radiation, or a combinations of these methods and subsequent detection of the carbon dioxide using IR spectroscopy or by conductometric or potentiometric techniques. The present invention is an improved process and apparatus for determining concentration levels of total organic and inorganic carbon compounds in aqueous samples.

Figure 1:
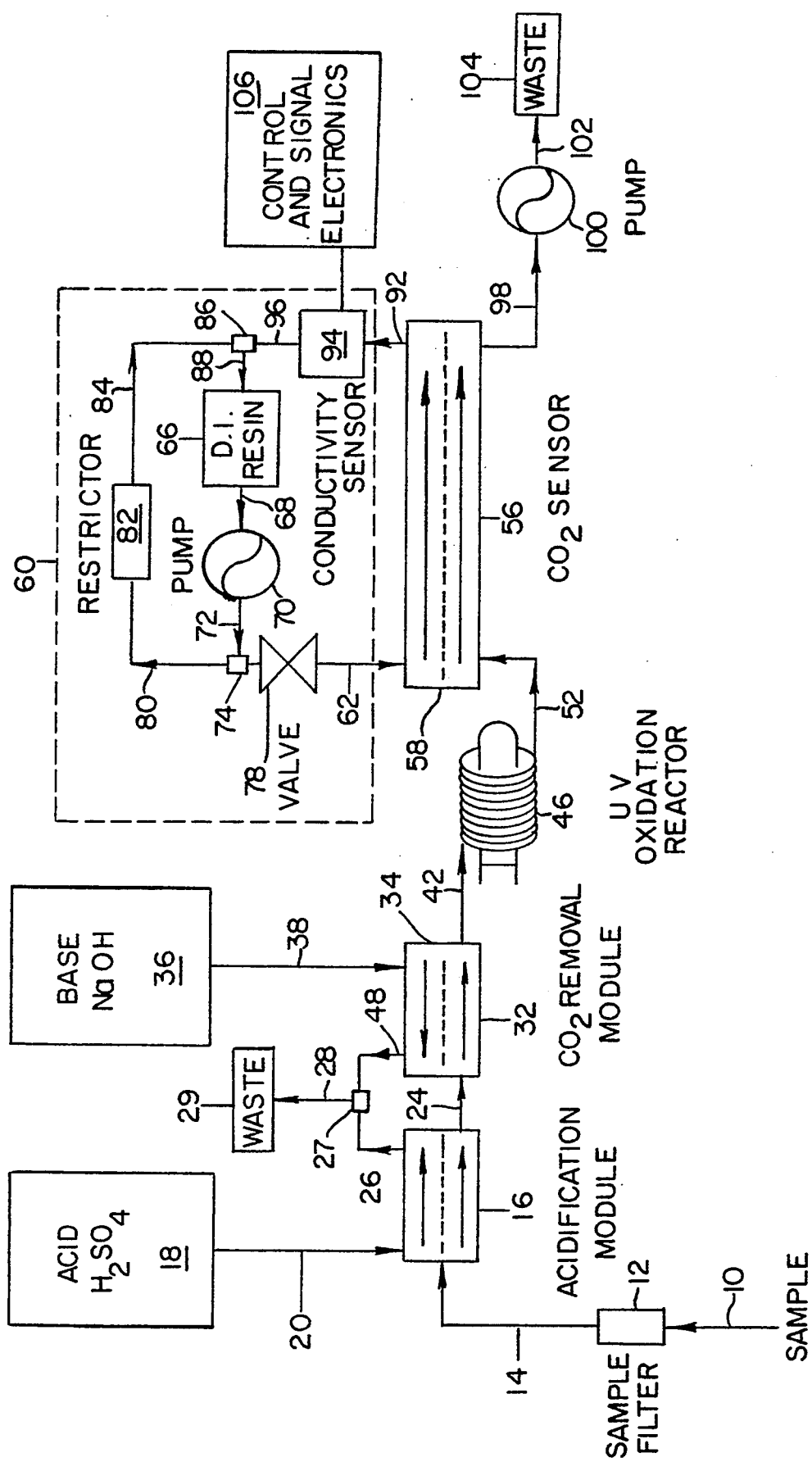
FIG. 1 is a block diagram depicting an embodiment of the present invention for the on-line measurement of total organic carbon concentrations with removal of inorganic carbon compounds.

A block diagram of one embodiment of the present invention is shown in FIG. 1. An aqueous sample inlet opening 10 is in communication with a particle filter 12 for the removal of particulate matter that may be suspended in the aqueous sample stream. A filter outlet conduit 14 is in fluid communication with the inlet of an acidification module 16. The water sample inlet of the acidification module 16 is in communication with a hollow acid permeable membrane (not shown) and permits passage of the sample stream through the inside of the hollow membrane. An acid reservoir 18 and acid inlet conduit 20 is in communication with a second inlet to the acidification module 16 which permits passage of the acid solution only around the outside of the hollow membrane. The flow rate of the aqueous acid from the reservoir 18 is maintained at a flow rate sufficient to cause diffusion of acid across the hollow membrane, and cause a reduction in the pH of the aqueous sample stream to a pH of less than about 2. The outlet of the hollow membrane is in communication with the aqueous sample outlet conduit 24 of the acidification module 16 and a second outlet conduit 26 is in communication with the area exterior to the hollow membrane that permits passage of the depleted aqueous acid solution to a tee 27 and, via conduit 28, to a suitable waste container.

The aqueous outlet conduit 24 from the acidification module is in communication with the aqueous sample inlet of the inorganic carbon removal module 32, which contains a gas permeable membrane 34 positioned such that the flowing aqueous sample stream passes on one side of the gas permeable membrane. An aqueous base reservoir 36 and base inlet conduit 38 is in communication with a second inlet to the inorganic carbon removal module 32, which is positioned such that the aqueous base stream passes on the opposite side of the gas permeable membrane from that of the aqueous sample. The flow of the aqueous base is countercurrent to that of the aqueous sample. The aqueous sample solution passes by means of the inorganic carbon removal module outlet conduit 42 to the aqueous sample inlet of the U.V. oxidation reactor 46. A second inorganic carbon removal module outlet 48 permits passage of the depleted aqueous base solution to a tee 27 via conduit 28 to a suitable waste container 29. The mixing of the deleted acid and base solutions in tee 27 minimizes any potential problems in the disposal of the waste streams.

A detailed description of the components of the U.V. oxidation reactor 46 are given below and shown in FIGS. 5–10. The U.V. oxidation module outlet conduit 52 is in communication with the aqueous sample inlet of the carbon dioxide sensor 56, which contains a gas permeable membrane 58 positioned such that the flowing aqueous sample stream passes on one side of the gas permeable membrane. A deionized water module 60 is in communication via the deionized water module outlet conduit 62 with the deionized water inlet of the carbon dioxide sensor 56 and the inlet is positioned to permit passage of deionized water on the opposite side of the gas permeable membrane from that of the aqueous sample stream. A relatively thin layer of deionized water (approximately 0.005") is maintained on the deionized water side of the gas permeable membrane to facilitate rapid analysis times.

The deionized water module consists of a mixed bed of anion and cation ion exchange resins 66 in communication via a conduit 68 with a circulating pump 70 which is in communication via a conduit 72 to a tee 74. One outlet of the tee 74 is in communication via conduit 76 with a solenoid shut-off valve 78, and the other outlet of the tee is in communication via a conduit 80 to a flow restrictor 82. The outlet of the solenoid shut-off valve is in communication via the deionized water outlet conduit 62 with the deionized water inlet of the carbon dioxide sensor 56. The outlet of the flow restrictor 82 is in communication via a conduit 84 to one inlet of a second tee 86 and the outlet of the tee is in communication via a conduit 88 to the inlet of the ion exchange resin bed 66.

The deionized water outlet of the carbon dioxide sensor 56 is in communication via a conduit 92 to the inlet of a micro-conductivity sensor 94. The outlet of the micro-conductivity sensor 94 is in communication via a conduit 96 to the other inlet of the second tee 86. The aqueous sample outlet of the carbon dioxide sensor 98 is in communication with the inlet of a peristaltic sampling pump 100, and the outlet of the sampling pump is connected via a conduit 102 to a suitable waste container 104. The micro-conductivity sensor 94 is connected to a suitable power supply (not shown) and the electrical output from the micro-conductivity sensor is connected to the control and signal electronics module 106.

The control and electronic module 106 is comprised of a computer or comparable electronic device which is capable of controlling the voltages and currents to all of the electrical components of the present invention, actuation of valves and switches in a pre-determined timed sequence, processing of the electrical signal from the micro-conductivity sensor and the calculation of total organic carbon concentration, total carbon concentration and total inorganic carbon concentration from output of the conductivity sensor.

Figure 2:
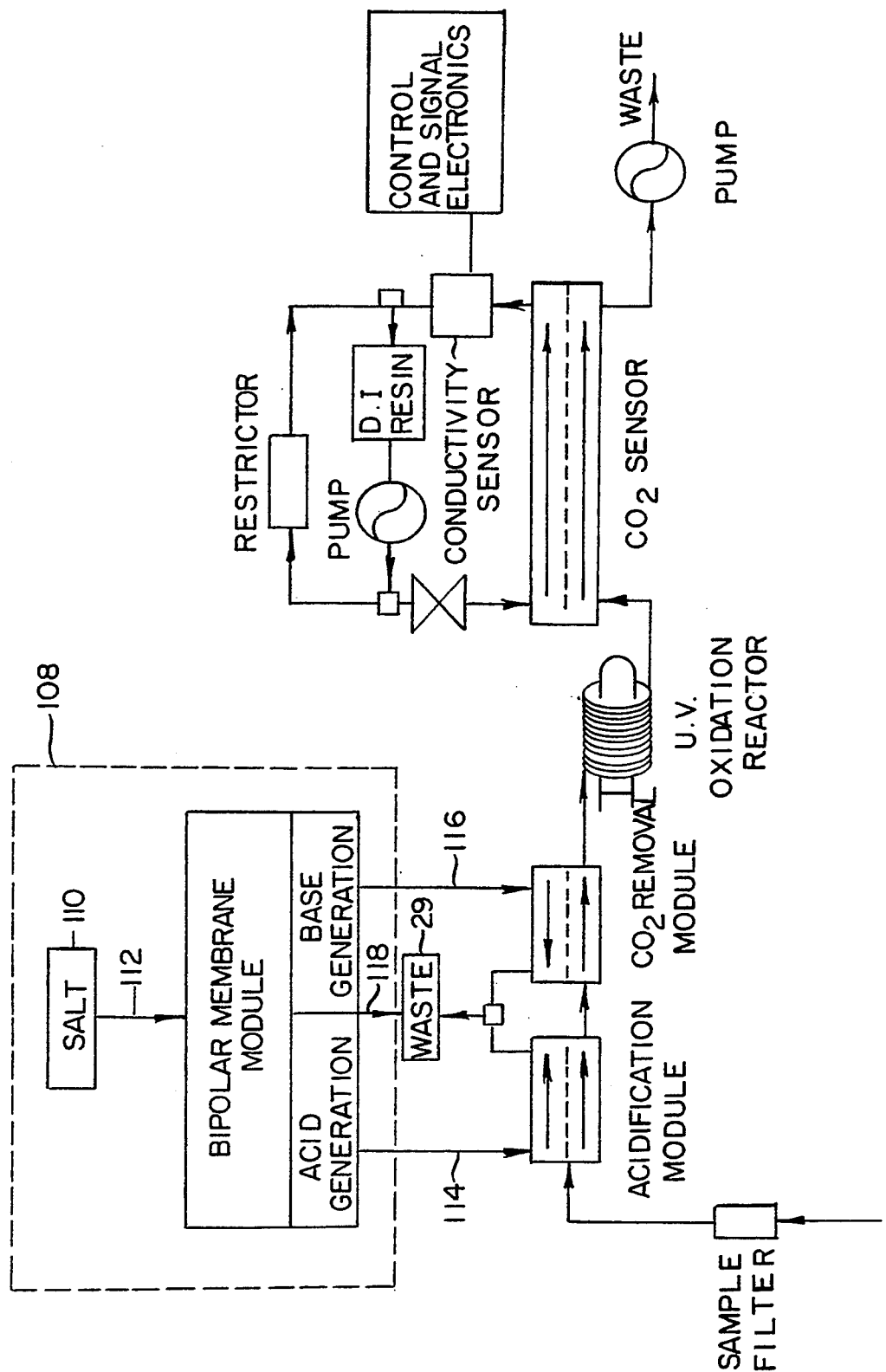
FIG. 2 is a block diagram depicting an embodiment of the present invention for the on-line measurement of total organic concentrations employing a bipolar membrane module for the generation of acid and base from an aqueous salt solution.

In an alternate embodiment of the present invention, shown in FIG. 2, the acid reservoir 18 and the aqueous base reservoir 36 are replaced with an acid/base generation module 108 which consists of an aqueous salt reservoir 110 which is in communication via conduit 112 with an electrodialysis system (not shown) which incorporates bipolar membranes, anion and cation ion exchange membranes and an electrical power supply for the production of separate streams of an aqueous acid, and aqueous base, and a depleted salt solution. The in-situ generated aqueous acid stream is in communication with the acid inlet of the acidification module via an acid inlet conduit 114. The in-situ generated aqueous base stream is in communication with the base inlet 40 of the inorganic carbon removal module via a base inlet conduit 116. The depleted salt solution is connected via a conduit 118 to a suitable waste container 29.

In operation of the present invention as described in FIGS. 1 and 2, the peristaltic sampling pump 100 withdraws an aqueous sample via the sample inlet opening 10, at a desired flow rate of approximately 50 to 100 microliters per minute into the acidification module 16. Aqueous acid, for example 3M phosphoric acid or 3M sulfuric acid, from the acid reservoir 18 or from the acid/base generation module 108 is passed through the acidification chamber, exterior to the hollow membrane, at a flow rate of approximately 5 uL/min. As the aqueous sample flows through the hollow membrane, some acid from the exterior of the membrane will diffuse into the aqueous sample and result in a decrease in the pH of the aqueous sample stream. The desired pH of the aqueous sample stream effluent of the acidification module is a pH of less than about 4.

After acidification, the aqueous sample stream enters the inorganic carbon removal module 32 via the aqueous sample inlet 30. Aqueous base, for example 3M sodium hydroxide, from the aqueous base reservoir 36 or from the acid/base generation module 108 is passed on one side of a gas permeable membrane 34, while the aqueous sample is passed on the opposite side. Carbon dioxide produced from the reaction of inorganic carbon species with the acid added to the aqueous sample stream in the acidification module 16 rapidly diffuses across the gas permeable membrane and into the aqueous base stream where it is converted into ionic species. The gas permeable membrane 34 is constructed of a material that will permit diffusion of carbon dioxide and other inorganic gases, but will not permit diffusion of organic acids and other volatile organic compounds.

The aqueous sample stream, after removal of the inorganic carbon compounds, enters the U.V. oxidation reactor 46, in which, using the methods and apparatus described below, organic compounds are converted to carbon dioxide and other products.

The aqueous sample stream effluent of the U.V. oxidation reactor 46 is directed via conduit 52 into the aqueous sample inlet of the carbon dioxide sensor 56, out through the aqueous sample outlet of the carbon dioxide sensor 98 through the peristaltic sample pump 100 to a suitable waste container 104.

A continuous supply of deionized water is produced in the deionized water module 60 by passing an aqueous stream of water through the mixed bed ion exchange resins 66 by means of the circulating pump 70 with the solenoid valve 78 in the closed position.

In the measurement cycle of the carbon dioxide sensor 56, the solenoid valve 78 is switched to the ON position to introduce a sample of deionized water via conduit 62 into the deionized water inlet of the carbon dioxide sensor 56. After a period of time (generally about 40 to 100 seconds), the solenoid valve 78 is returned to the OFF position. As the sample stream passes on one side of the gas permeable membrane 58 of the carbon dioxide sensor 56, the carbon dioxide formed in the U.V. oxidation module 46 will diffuse across the gas permeable membrane into the deionized water sample on the opposite side of the membrane, where the carbon dioxide will be converted into ionic species. After a short period of time (generally about 5 min.) an equilibrium will be established between the concentration of carbon dioxide in the flowing aqueous sample stream and the deionized water sample across the gas permeable membrane.

After this equilibration period, the solenoid valve 78 is switched to the ON position and the deionized water sample is passed into the micro-conductivity cell 94 by means of the circulating pump 70. The increase in conductivity caused by the presence of ionic species formed from carbon dioxide is measured by the micro-conductivity cell 94 and associated control and signal module 106. The observed increase in the conductivity of the deionized water sample can be directly related to the concentration of carbon dioxide present in the aqueous sample stream, and hence, the level of organic compounds present in the aqueous sample stream by known means.

As the conductivity of the deionized water sample is being determined, the equilibration period for the next measurement cycle is underway. Thus, in the present invention, the measurement of the organic composition of an aqueous sample stream can be determined about every five minutes, or at any longer desired measurement interval.

Figure 3:
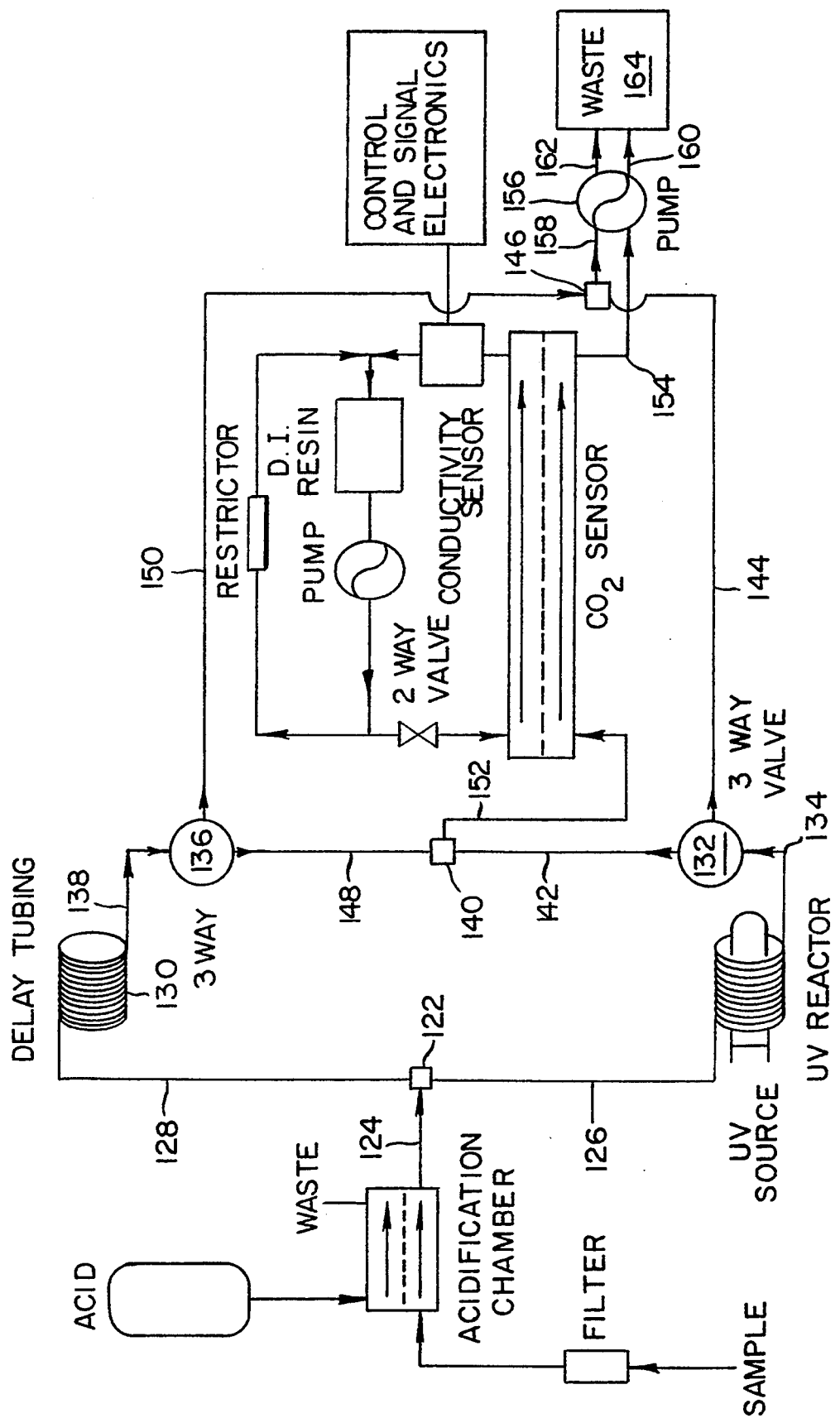
FIG. 3 is a block diagram depicting an embodiment of the present invention for the on-line measurement of both total organic and inorganic carbon concentrations, employing a stream splitting technique.

An additional embodiment of the present invention is illustrated in FIG. 3 for the determination of both total organic and total inorganic carbon concentration in an aqueous sample stream. In this embodiment of the invention, the inorganic carbon removal module 32 is replaced with a sample stream splitter 122. The aqueous sample effluent of the acidification module 16 is in communication with sample stream splitter 122 via conduit 124.

Approximately one-half of the aqueous sample stream is passed from the outlet of the sample stream splitter 122 to the aqueous sample inlet of the U.V. oxidation reactor 46 via conduit 126. The remainder of the aqueous sample stream from the outlet of the sample stream splitter 122 is in communication via conduit 128 with the inlet of the delay tubing coil 130. The outlet of the U.V. oxidation reactor 46 is in communication with the total carbon three-way valve 132 via conduit 134 and the outlet of the delay tubing coil 130 is in communication with a second, total inorganic carbon three-way valve 136 via conduit 138.

One outlet of the total carbon three-way valve 132 is in communication with one inlet of the carbon dioxide sensor inlet tee 140 via conduit 142, and the second outlet of the three-way valve is in communication via conduit 144 to one inlet of the pump inlet tee 146. Similarly, one outlet of the total inorganic carbon three-way valve 136 is in communication with the carbon dioxide inlet sensor tee 140 via conduit 148, and the second outlet of the three-way valve is in communication with the pump inlet tee 146 via conduit 150.

The outlet from the carbon dioxide inlet tee 140 is in communication with the aqueous sample stream inlet of the carbon dioxide sensor 56 via conduit 152 and the aqueous sample outlet of the carbon dioxide sensor 56 is in communication via conduit 154 with the inlet of the peristaltic sampling pump 156.

The outlet of the pump inlet tee is also in communication via conduit 158 with the inlet of the peristaltic pump. In contrast with the apparatus described in FIGS. 1 and 2, the peristaltic sampling pump 156 employed in this embodiment of the invention is used to sample two separate aqueous streams simultaneously, the aqueous outlet of the carbon dioxide sensor 56 via conduit 154 and the outlet of the pump inlet tee 146 via conduit 158. The pump outlet from both aqueous sample streams is passed through conduits 160 and 162 to a suitable waste container 164.

In operation, this embodiment of the invention employs to separate measurement cycles; the measurement of the total inorganic carbon concentration of the aqueous sample and the measurement of the total carbon concentration (total organic and total inorganic carbon) of the aqueous sample. The total organic carbon concentration of the sample is then computed from the difference between these two measurements. As described above, the peristaltic sampling pump 156 is used to draw the aqueous sample from the sample inlet 10, through particle filter 12 and through the acidification module 16. The aqueous sample then enters the sample stream splitter 122 which diverts approximately equal liquid flows through conduits 126 and 128.

In the total inorganic carbon measurement cycle, the total inorganic carbon three-way valve 136 is positioned such that the aqueous sample stream flows through conduit 148 to the carbon dioxide sensor inlet tee 140, with no liquid flow passing through conduit 150. The total carbon three-way valve 132 is positioned such that the aqueous sample stream flows through conduit 144 to the peristaltic pump inlet tee 146, thus bypassing the carbon dioxide sensor 56.

As described above, a flow of deionized water from the deionized water module 60 is introduced into the deionized water inlet of the carbon dioxide sensor 56 by positioning the solenoid valve 78 in the ON position and the flow of deionized water terminated by positioning the solenoid valve 78 in the OFF position. Carbon dioxide formed from the reaction of inorganic carbon species with the acid from the acidification module 16 will rapidly diffuse across the gas permeable membrane 58 of the carbon dioxide sensor 56 resulting in an increase in the conductivity of the deionized water, which is subsequently measured by the micro-conductivity sensor 94. This increase in conductivity can be directly related to the concentration of inorganic carbon species in the aqueous sample by known means.

After the measurement of total inorganic carbon is complete (generally about 5 min.), the apparatus is reconfigured for the measurement of the concentration of total carbon compounds in the aqueous sample. The total carbon three-way valve 132 is positioned to permit flow of the aqueous sample via conduit 142 go to the inlet tee of the carbon dioxide sensor 140, with no liquid flow through conduit 144. The total inorganic carbon three-way valve 136 is positioned to permit flow of the aqueous sample via conduit 150 to the peristaltic pump inlet tee 146.

As the aqueous sample stream passes through the acidification module 16, inorganic carbon species will be converted to carbon dioxide, while organic compounds remain unreacted. In the U.V. oxidation module 46, the organic compounds will be converted to carbon dioxide, thus the level of carbon dioxide in the aqueous sample stream passing through the carbon dioxide sensor 56 will be directly proportional to the concentration of both organic carbon compounds and inorganic compounds in the original sample.

The measurement of the total carbon content of the aqueous sample stream entering the carbon dioxide sensor 56 is conducted in the same manner as described above. After measurement of the total carbon concentration and total inorganic carbon concentration, the total organic carbon concentration is computed as the difference between these two values.

In this embodiment of the invention, the concentration of total carbon, total inorganic carbon, and total organic carbon can generally be determined approximately every ten minutes or at longer intervals if desired.

Figure 4:
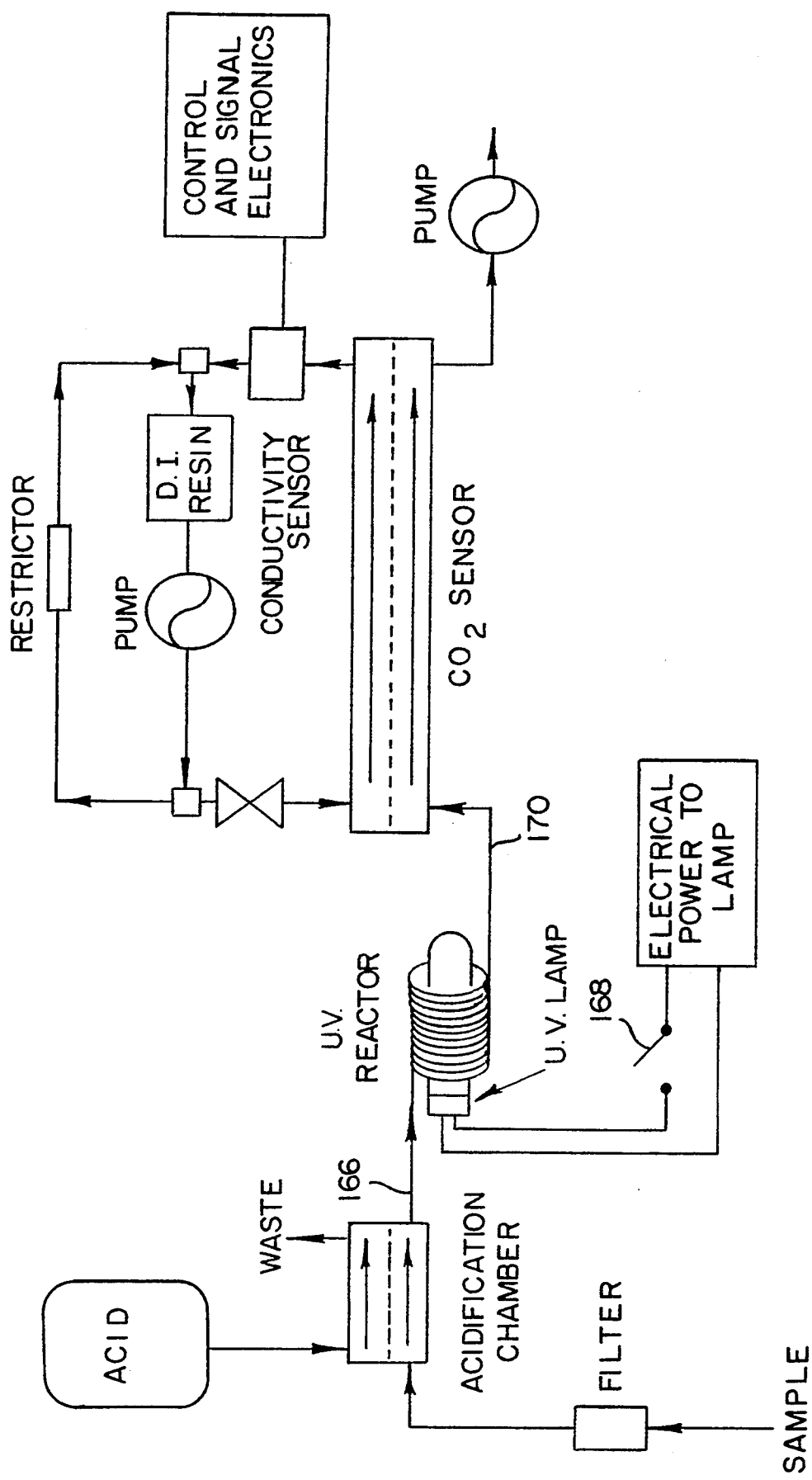
FIG. 4 is a block diagram depicting an embodiment of the present invention for the on-line measurement of both total organic and inorganic carbon concentrations without stream splitting.

In another embodiment of the invention, the concentration of total carbon compounds, total organic carbons and total inorganic carbon compounds is determined using the apparatus shown in FIG. 4. In this embodiment, the sample stream splitter 122 is replaced with a conduit 166 which permits passage of the aqueous sample from the outlet of the acidification module 16 to the inlet of the U.V. oxidation module 46. The U.V. oxidation module 46 is equipped with an electrical power switch 168. The aqueous sample stream outlet of the U.V. reactor module 46 is in communication with the aqueous sample inlet of the carbon dioxide sensor 56 via conduit 170.

In operation, the peristaltic sampling pump 100 is used to withdraw the aqueous sample via the sample inlet 10, through the particle filter 12 and acidification module 16 as described above. For the measurement of total inorganic carbon compounds in the sample, the electrical power to the U.V. oxidation reactor 46 is discontinued by positioning the electrical power switch 168 in the OFF or OPEN position. Under these conditions, organic compounds will not be converted to carbon dioxide in the U.V. oxidation module. Inorganic carbon species, however, will react with the acid from the acidification module to form carbon dioxide. The effluent of the U.V. oxidation module 46 is passed into the carbon dioxide sensor and the concentration of inorganic carbon species in the aqueous sample is determined using the procedure described above.

After completion of the measurement of the total inorganic carbon concentration (generally about 5 min.), the electrical power to the U.V. oxidation module 46 is restored by positioning the electrical power switch 168 in the ON or CLOSED position. As will be described below, with electrical power, organic compounds present in the aqueous sample will be converted to carbon dioxide and other products. The effluent of the U.V. oxidation reactor 46 will therefore contain carbon dioxide from both organic and inorganic compounds and the concentration of total carbon species in the aqueous sample is measured by the carbon dioxide sensor 56 as described above. The concentration of total organic compounds in the aqueous sample is then computed as the difference between the total carbon content and the total inorganic carbon content.

As shown in FIGS. 1–4, a major component of the present invention is an U.V. reactor module 46. In this present disclosure, several embodiments of the U.V. reactor module are described. Each reactor design offers significant advantages over the prior art, and each of the embodiments may be preferred depending on the particular application of the apparatus. Each design, as will be discussed below, offers advantages in terms of simplicity, use of chemical reagent systems, and application to the wide range of total organic carbon concentrations present in water samples as diverse as high purity process waters using the electronics industry, to municipal and industrial waste waters. Each of the U.V. reactor modules described below can be used in conjunction with the embodiments shown in FIGS. 1–4, depending upon the nature of the aqueous sample stream and the requirements of the analyst.

Figure 5:
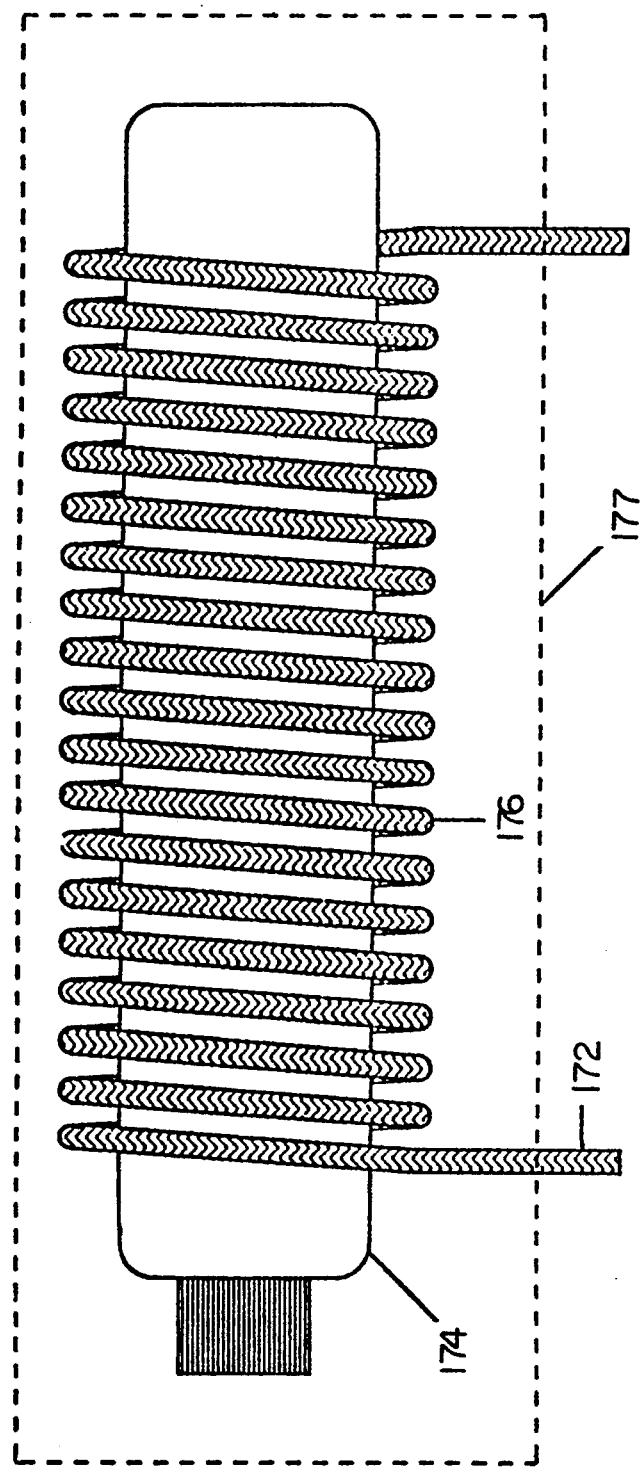
FIG. 5 is a schematic representation of the semiconductor-packed photoreactor module of the present invention.

FIG. 5 is illustrative of a simple U.V. oxidation module for use with the present invention. The aqueous sample inlet of the U.V. oxidation module is in communication with a coiled fused silica tube 172 of approximately 120 cm in length and with an internal diameter of approximately 1 mm. The radius of the coil is such that a U.V. radiation source 174 can be positioned in the annular region of the fused silica coiled tube 172. A suitable power supply and electrical connections (not shown) are used for the operation of the U.V. radiation source 174, which may consist of any known device which emits U.V. radiation, such as a gas discharge tube or mercury vapor discharge tube. The entire irradiated length of the fused silica coiled tube 172 is packed with an n-type semiconductor coated on a suitable support material 176, held in place by a retaining system such as quartz wool plugs (not shown) to form the semiconductor-packed photoreactor 177. Any n-type semiconductor with a band gap greater than about 2 eV may be employed for this embodiment of the invention, for example $TiO_2$, SiC, ZnO, CdS. U.V. transparent material, for example silica gel, quartz beads, may be used as the support. In one embodiment of the U.V. oxidation module, $TiO_2$ particles supported on silica gel were used for the oxidation of a range of organic compounds to form carbon dioxide, which was subsequently measured using the carbon dioxide sensor 56. As described in Background of the Invention above, n-type semiconductors are known to serve as catalysts for the photooxidation of organic compounds in aqueous solution. The design of the U.V. oxidation module shown in FIG. 5 has been demonstrated to provide high efficiency conversion of organic compounds to form carbon dioxide from aqueous samples at concentrations up to about 10 mg/L total organic carbon, without the addition of oxygen or other chemical reagents. The simplicity of the design of this U.V. oxidation module is thus a preferred embodiment of the invention for the measurement of total organic carbon in aqueous sample streams containing lower levels ($\leq 10$ mg/L) of organic compounds.

Figure 6:
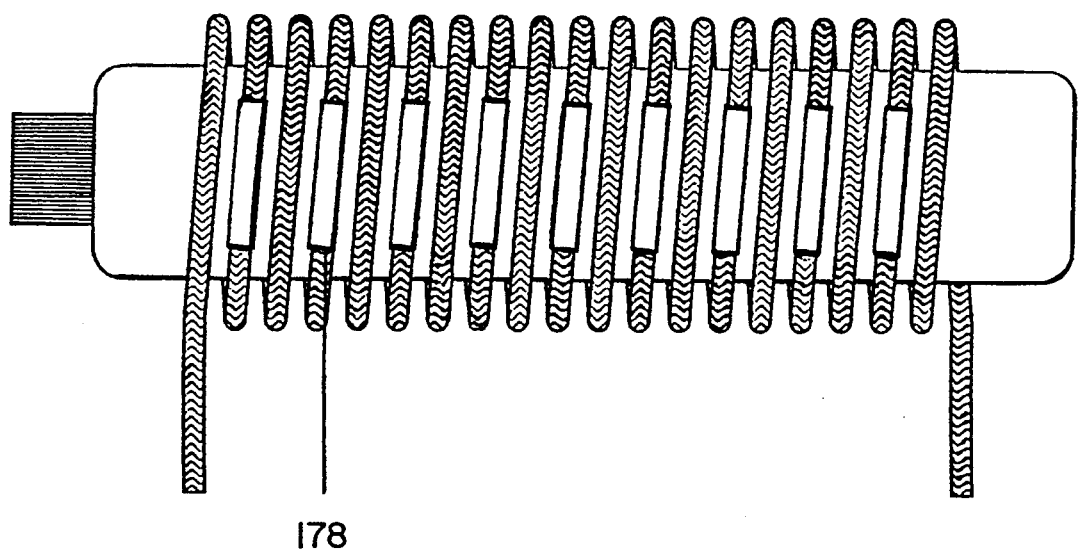
FIG. 6 is a schematic representation of the semiconductor-packed photoreactor module of the present invention incorporating sections of palladium tubing for hydrogen removal.

For the determination of total organic carbon in aqueous samples in concentrations that are above 10 mg/L, the apparatus shown in FIG. 5 may not be suitable, due to the lack of sufficient concentrations of an oxidizing agent. The measurement range of the present invention can be extended to concentrations greater than 10 mg/L organic carbon if the embodiment of the apparatus shown in FIG. 6 is employed. In this apparatus, the coiled fused silica tube 172 has been modified to include short lengths of palladium tubing 178. The U.V. reactor 179 shown in FIG. 6 is operated under conditions that will result in the formation of oxygen and hydrogen from the photolysis of water. The in-situ generated oxygen is then employed, in addition to the semiconductor catalyst 176, in the conversion of organic compounds to form carbon dioxide. The embodiment of the invention shown in FIG. 6 permits the measurement of total organic carbon in aqueous samples at concentrations greater than 10 mg/L without the addition of any chemical reagents from external sources. As noted in the Background of the Invention, hydrogen gas rapidly diffuses through palladium metal and therefore the addition of short segments of palladium tubing permits rapid removal of hydrogen generated from the photolysis of water from the aqueous stream. A hydrogen exhaust conduit (not shown) is used to remove the gas from the U.V. reactor module.

Figure 7:
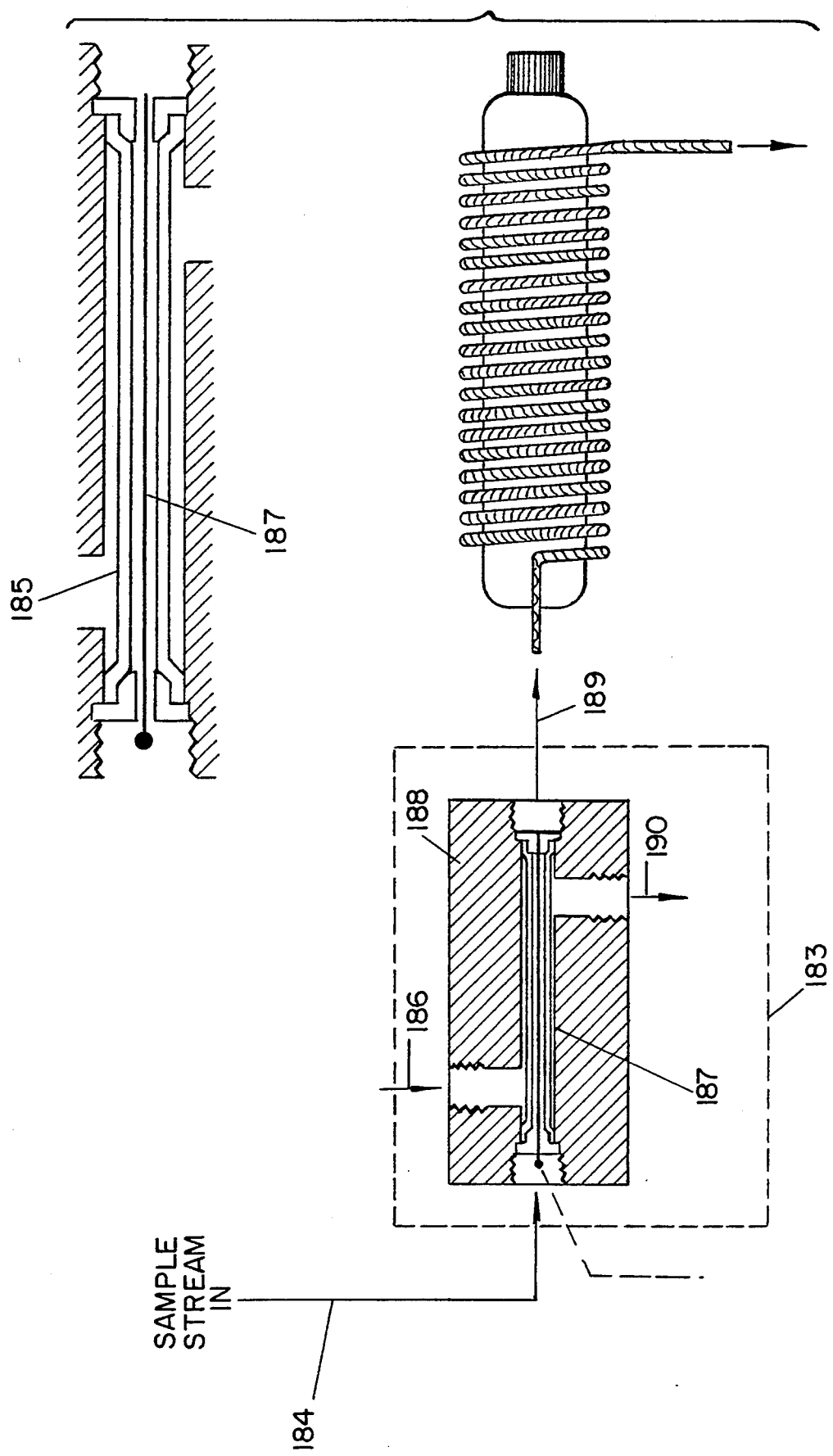
FIG. 7 is a schematic representation of an in-line electrolytic oxygen generator and semiconductor-packed photoreactor module of the present invention.

A third embodiment of the U.V. oxidation module is shown in FIG. 7 and incorporates an electrolysis module 183 for the generation of oxygen prior to the semiconductor catalyzed photoreactor. In FIG. 7, the sample inlet conduit 184 represents either the aqueous sample stream effluent from the inorganic carbon removal module (conduit 42 in FIGS. 1 and 2), the aqueous sample stream effluent from the sample stream splitter (conduit 126 in FIG. 3), or the aqueous sample stream outlet of the acidification module (conduit 166 in FIG. 4). The sample inlet conduit 184 is in communication with the aqueous sample inlet of the electrolysis module 183 which contains a hollow electrolyte permeable membrane 185. The aqueous sample inlet of the electrolysis module is positioned such that the sample stream passes through the annular region of the membrane. A second fluid stream containing ionic compounds suitable for the conduction of electrical current through solution (electrolyte) is passed into the electrolysis module 183 via conduit 186 and this electrolyte solution inlet is positioned such that the electrolyte solution passes over the exterior of the membrane 185. In this embodiment of the U.V. oxidation module, a suitable source of the electrolyte solution is the water stream(s) from the acidification module 26, the inorganic carbon removal module 48, or an external aqueous salt solution.

A platinum electrode 187 is positioned in the interior of the hollow membrane and the outer case of the electrolysis module is constructed from a suitable metal 188 and covered with an electrical insulating material. Electrical connections (not shown) are in contact with the platinum electrode and the metal case of the module and are connected to a suitable power supply (not shown).

In operation, a electrical potential sufficient to cause the electrolysis of water is applied between the platinum electrode and the metal case of the electrolysis module. Under these conditions, the platinum electrode serves as the anode for the generation of molecular oxygen from the aqueous sample in the interior of the hollow membrane. The oxygen-containing sample stream is then passed via conduit 189 to the inlet of the semiconductor-packed photoreactor 177, described in FIG. 5. The metal case of the electrolysis module serves as the cathode in this electrolysis reaction and hydrogen gas that is generated is removed from the electrolysis module via the electrolyte outlet 190.

The electrolysis module 183 permits generation of oxygen at concentrations much greater than the dissolved oxygen levels in aqueous samples or the concentrations of oxygen that can be generated by semiconductor-catalyzed photolysis of water. Thus the embodiment of the U.V. reactor module illustrated in FIG. 7 permits the measurement of higher concentration levels of total organic carbon in aqueous samples than can be achieved using the U.V. reactor modules described in FIGS. 5 and 6, but requires the addition of an external power supply and an electrolyte stream.

The placement of the electrolysis module prior to the U.V. radiation source offers significant advantages over the disclosure of Winkler. The use of a membrane to separate the anode and cathode is incorporated in the present design and was described by Winkler. However, in Winkler's device, the U.V. radiation source is an integral part of the electrolysis system. Electrolyte permeable membranes such as Naphion, are known to undergo photo-decomposition upon exposure to U.V. radiation. Thus, in the invention described by Winkler, significant levels of organic compounds and carbon dioxide are added to the aqueous sample stream from the decomposition of the membrane. In the present invention, the membrane is not exposed to U.V. radiation and, therefore, the potential of organic compound contamination of the sample stream is eliminated.

In the embodiments of the U.V. oxidation reactor described, oxidation of organic compounds to form carbon dioxide is based solely on semiconductor-catalyzed oxidation combined with photolytic or electrolytic generation of oxygen. For aqueous samples containing higher levels of total organic compounds ($\geq 30$ mg/L), it is desirable to use an additional chemical oxidizing agent such as persulfate ion. As previously noted, this reagent is widely used in the prior art, but as noted above, aqueous solutions of this reagent undergo decomposition and, as a consumable reagent, frequent preparations of aqueous solutions of persulfate are required for methods and apparatus employing this reagent for the oxidation of organic compounds to form carbon dioxide. As is also noted above, the reagent can be generated, in-situ, by the electrolysis of aqueous solutions of sulfate ion. Thus, an improvement over existing devices for the measurement of total organic carbon content of aqueous solutions can be achieved using a combination of in-situ generation of the persulfate reagent, coupled with or without semiconductor-catalyzed photo-oxidation.

Figure 8:
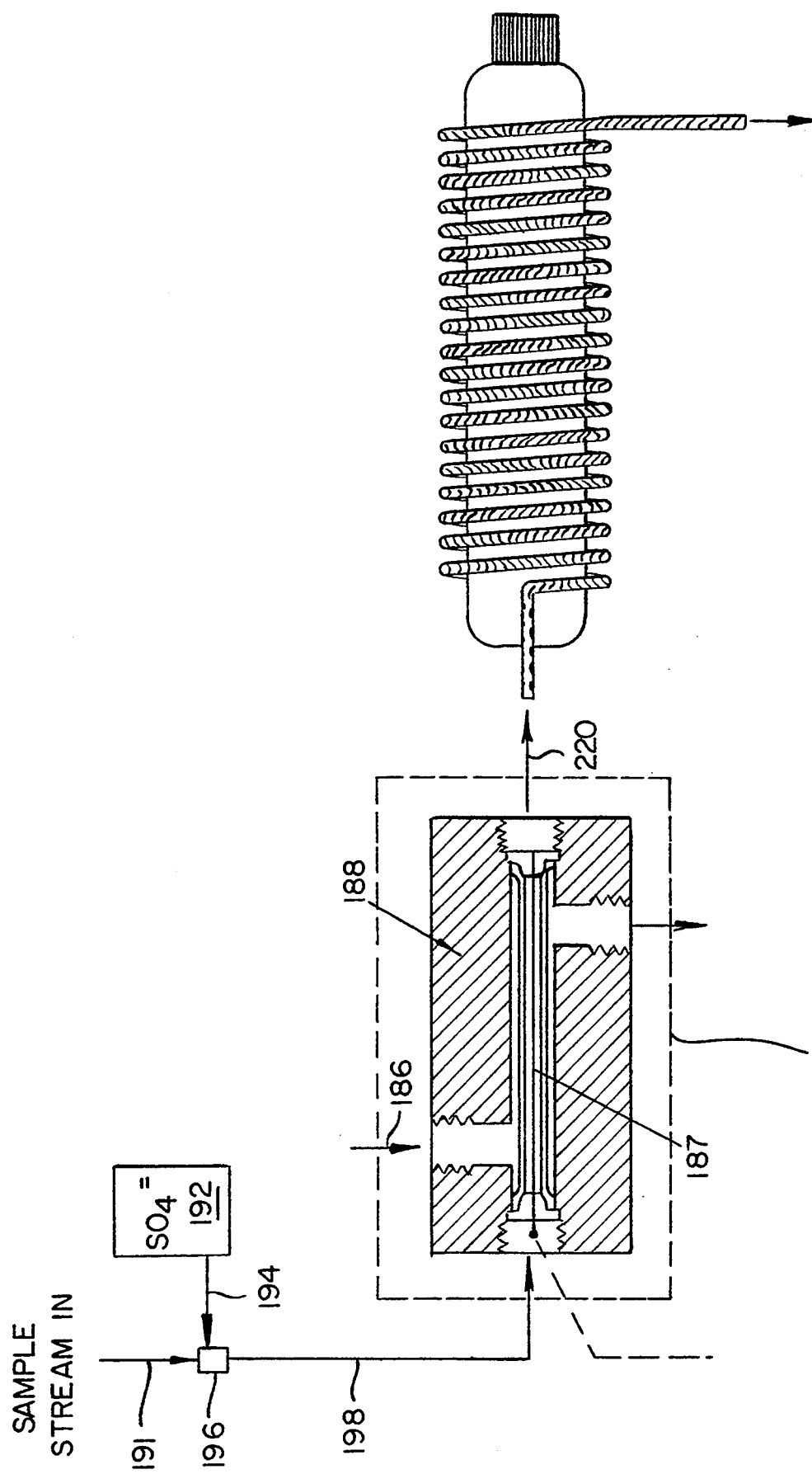
FIG. 8 is a schematic representation of an in-line electrolysis module for the generation of persulfate, hydrogen peroxide and oxygen and for use with semiconductor-packed photoreactor module of the present invention.

Accordingly, an additional embodiment of the U.V. oxidation module, shown in FIG. 8, combines in-situ generation of persulfate with the previously described semiconductor photoreactor.

In FIG. 8, the sample inlet conduit 191 represents the aqueous sample stream effluent as described for conduit 184 in FIG. 7. A sulfate reservoir 192 is in communication via conduit 194 with one inlet to a mixing tee 196, and the aqueous sample stream is in communication with a second inlet to the mixing tee 196 via conduit 191. The outlet of the mixing tee 196 is in communication via conduit 198 with the aqueous sample inlet of the persulfate generation module 200. The outlet of the persulfate generation module is in communication via conduit 220, with the inlet of the semiconductor-packed photoreactor 177. The components of the persulfate generation module including the hollow membrane, platinum electrode, metal outer casing, electrolyte solution and external power supply are the same as described above for FIG. 7. In operation, however, the principal electrochemical reactions occurring in the persulfate generation module are fundamentally different.

As noted in the discussion of prior art, Smit and Hoogland have demonstrated that application of an electrical potential greater than about $-2.1$ V versus the standard hydrogen electrode to an aqueous solution of sulfate ions will result in the formation of persulfate, hydrogen peroxide and molecular oxygen at the anode and production of hydrogen at the cathode. In the embodiment of the invention shown in FIG. 8, a reservoir containing 1 to 3M of a sulfate salt or sulfuric acid is added to the aqueous sample stream prior to entrance into the electrolysis module. In the electrolysis module, persulfate, hydrogen peroxide and oxygen are produced at the platinum electrode and hydrogen gas produced at the outer metal housing (cathode) of the module. The persulfate, hydrogen peroxide, and oxygen are transported along with the flowing aqueous sample stream into the semiconductor-packed photoreactor 177. This combination of in-situ generated chemical oxidizing agents and semiconductor-catalyzed photo-oxidation of organic compounds to form carbon dioxide provides highly efficient conversion of organic compounds to carbon dioxide, for the determination of total organic carbon concentrations in aqueous samples as high as 100 mg/L carbon.

Figure 9:
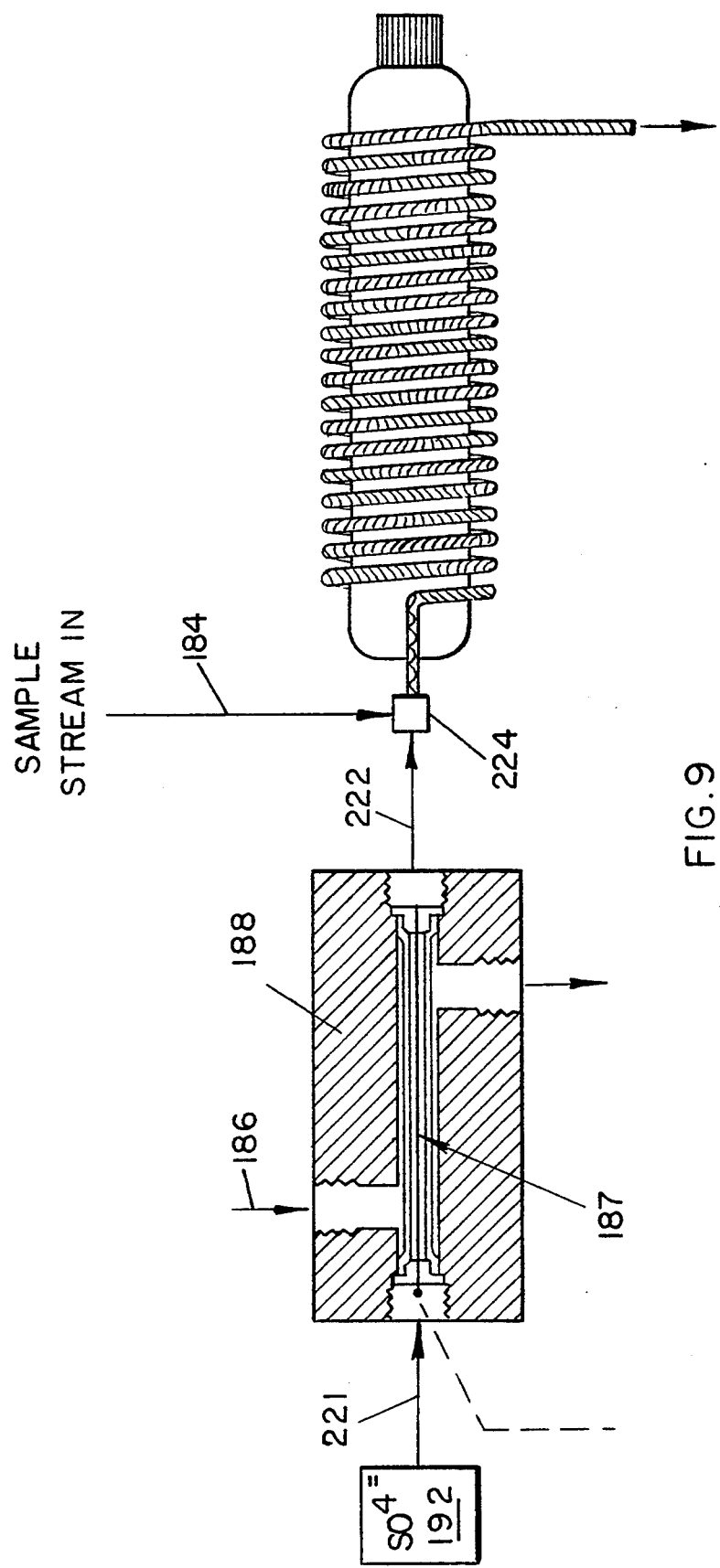
FIG. 9 is a schematic representation of an off-line electrolysis module for the generation of high concentrations of persulfate for use with the semiconductor-packed photoreactor module of the present invention.

The next embodiment of the U.V. reactor module for this invention is shown in FIG. 9. In this design, the effluent of the sulfate ion reservoir 192 is in communication with the electrolysis module 200 via conduit 221. The operation of the electrolysis module is identical with that described above for FIG. 3c, however, the concentration of sulfate ions entering the electrolysis module is much greater in the design shown in FIG. 9 than shown in FIG. 8, thus resulting in the generation of higher concentrations of persulfate in the electrolysis module. The outlet of the electrolysis module is in communication via conduit 222 with one inlet of a mixing tee 224. The aqueous sample inlet 184 is in communication with the second inlet of the mixing tee 224 and the outlet of the mixing tee is in communication via conduit 226 with the inlet of the semiconductor-packed photoreactor 177.

Using the higher concentration of persulfate generated in the embodiment of the invention shown in FIG. 9, where the electrolysis module is off-line, determination of the total organic carbon content at concentrations as great as 1000 mg/L can be achieved.

Figure 10:
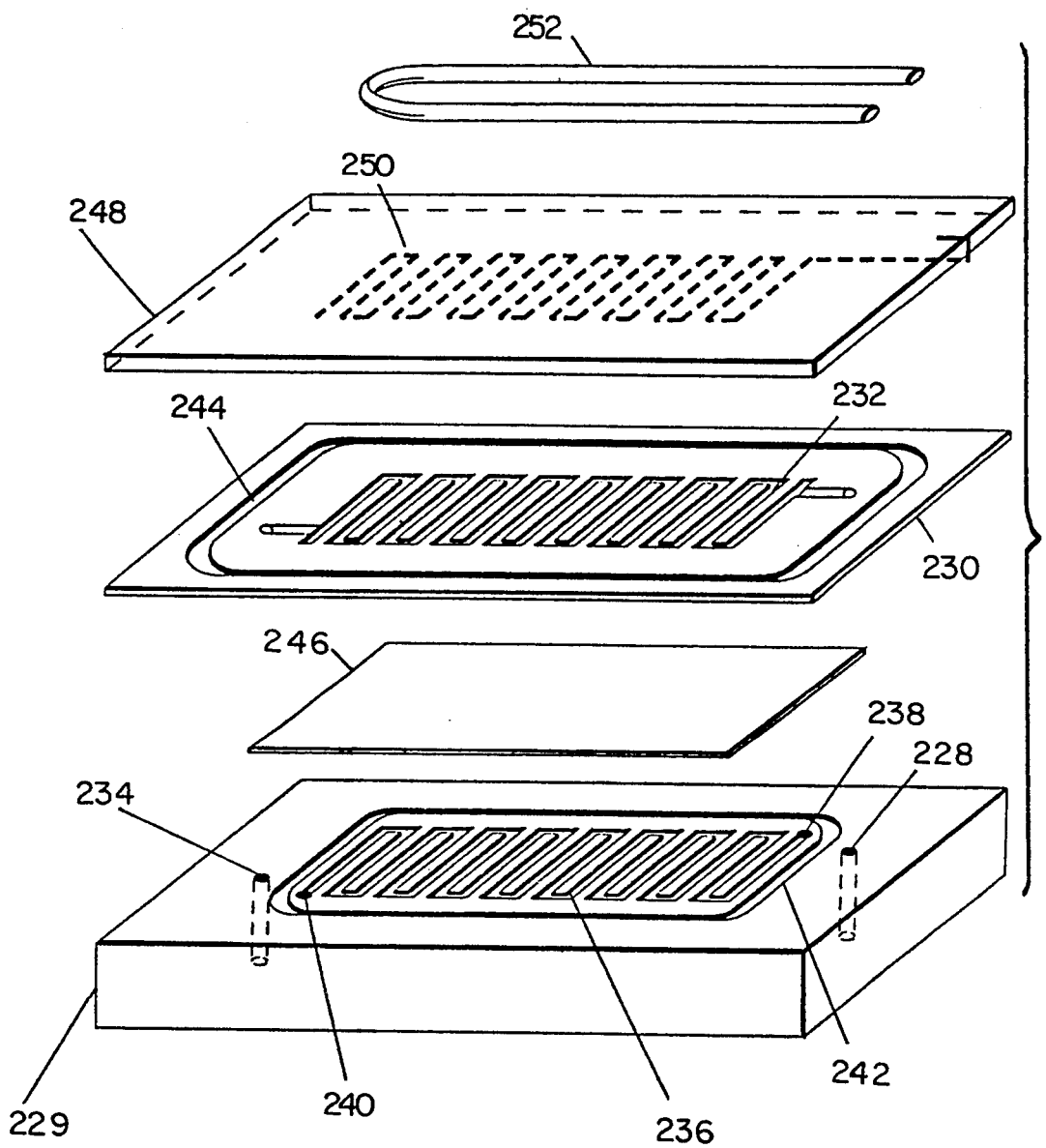
FIG. 10 is a schematic representation of the combined in-situ electrolysis module and photo-oxidation reactor of the present invention.

A final embodiment of the U.V. oxidation module of present invention is shown in FIG. 10. In this embodiment, electrolytic generation of the oxidizing agents is conducted in the U.V. photoreactor chamber. A sample inlet 228 which represents either the aqueous sample effluent from the inorganic carbon removal module (conduit 42 in FIGS. 1 and 2), the aqueous sample stream effluent from the sample stream splitter (conduit 126 in FIG. 3), the aqueous sample stream outlet of the acidification module (conduit 166 in FIG. 4) or the effluent from the sulfate solution mixing tee (conduit 198 in FIG. 8) is located in the bottom of a pressure plate assembly 229. A ceramic spacer plate 230 is in direct communication with the aqueous sample inlet portion of the pressure plate assembly. A serpentine groove 232, approximately 0.02 inches in depth, is cut into the ceramic spacer to provide a flow path for the aqueous sample through the oxidation module. The outlet of the ceramic spacer is in direct communication with a sample outlet 234 located in the pressure plate assembly. The sample outlet 234 is in direct communication with the aqueous sample inlet of the carbon dioxide sensor 46 via conduit 52. A matching serpentine gas flow channel 236 is machined into the pressure plate assembly and is in communication with a purge gas inlet 238 and a purge gas outlet 240. An external purge gas source is in communication with the purge gas inlet 238 and an inert gas (e.g., nitrogen, helium, etc.) or an air source can be employed. Grooves for the placement of O-rings (not shown) are machined into the pressure plate assembly 242 and the ceramic spacer plate 244 for the purpose of providing gas and liquid tight seals in the U.V. reactor module design. A thin sheet of palladium metal 246 is positioned between the pressure plate assembly and the ceramic spacer plate. A fused silica plate 248 is positioned above the ceramic spacer plate and a platinum metal 250 is deposited in a matching serpentine pattern on the lower side of the fused silica plate. A U.V. radiation source 252 is positioned directly above the fused silica plate, and the entire assembly housed in an electrically insulated and light-tight container (not shown).

A suitable power supply and electrical connections (not shown) are used for the operation of the U.V. radiation source. A second power supply and electrical connections (not shown), capable of producing voltages and currents sufficient for the electrolysis of water and for the oxidation of sulfate to persulfate is employed to provide an electrical potential between the platinum trace on the fused silica plate 250 and the palladium metal sheet 246.

In operation, the serpentine groove in the ceramic spacer 232 may be packed with the semiconductor-catalysts described above or may be operated without the use of a catalyst. A purge gas flow rate of about 1 to 10 mL per minute is passed through the gas flow channel 236 and an aqueous sample flow rate of about 10 to 100 microliters per minute is passed through the sample inlet 228.

As described above, the application of an electrical potential between the platinum anode and the palladium cathode will result in the production of oxygen in the presence of water, or hydrogen peroxide and persulfate in the presence of sulfate ion, at the anode and hydrogen gas at the palladium cathode. The hydrogen gas will rapidly diffuse through the thin palladium sheet into the purge gas channel and be rapidly removed from the system. The in-situ generated oxidizing agents combined with semiconductor-catalyzed photolytic reactions (or uncatalyzed, direct U.V. photolysis) permits rapid oxidation of the organic compounds to form carbon dioxide.

This embodiment of the present invention offers significant improvements over the system described by Winkler. In contrast with Winkler's device which requires a solid, polymeric electrolyte, the design of the invention as described in FIG. 10 contains no organic carbon containing materials.

Figure 11:
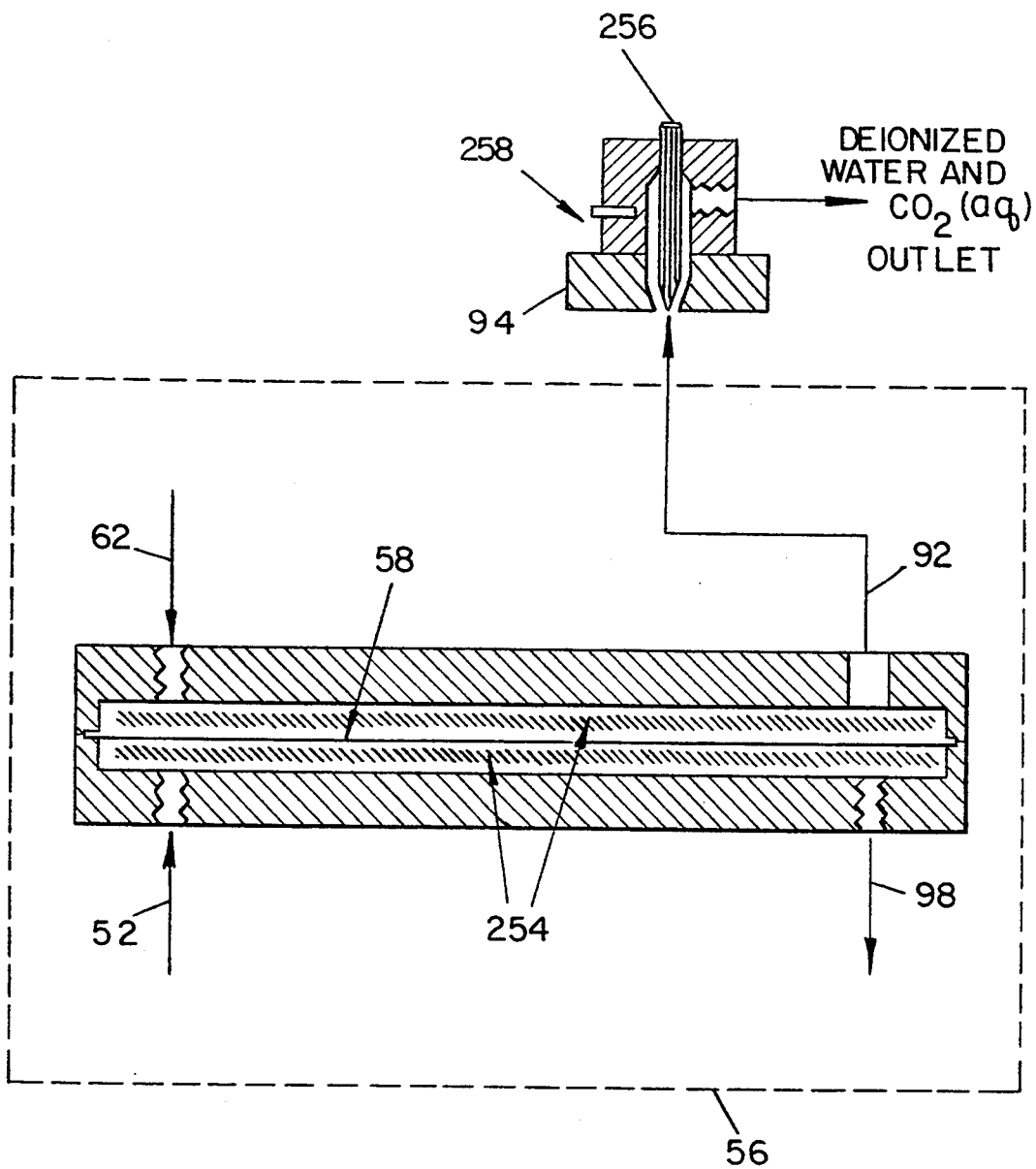
FIG. 11 is a schematic representation of the carbon dioxide sensor component of the present invention.

A more detailed description of the carbon dioxide sensor 56 component of the present invention is shown in FIG. 11. The carbon dioxide selective membrane 59 is positioned between two stainless steel meshes 254. These mesh elements support the carbon dioxide selective membrane and also facilitate mixing in the two aqueous solutions by producing turbulent flow. As explained in the description of the operation of the carbon dioxide sensor in the discussion of FIG. 1, conduit 92 is used to transfer the carbon dioxide containing aqueous stream into the micro-conductivity cell 94 for subsequent measurement. The micro-conductivity cell includes a conductivity electrode 256 and temperature sensor 258 used for temperature compensation in the conductivity measurement.

Figure 12:
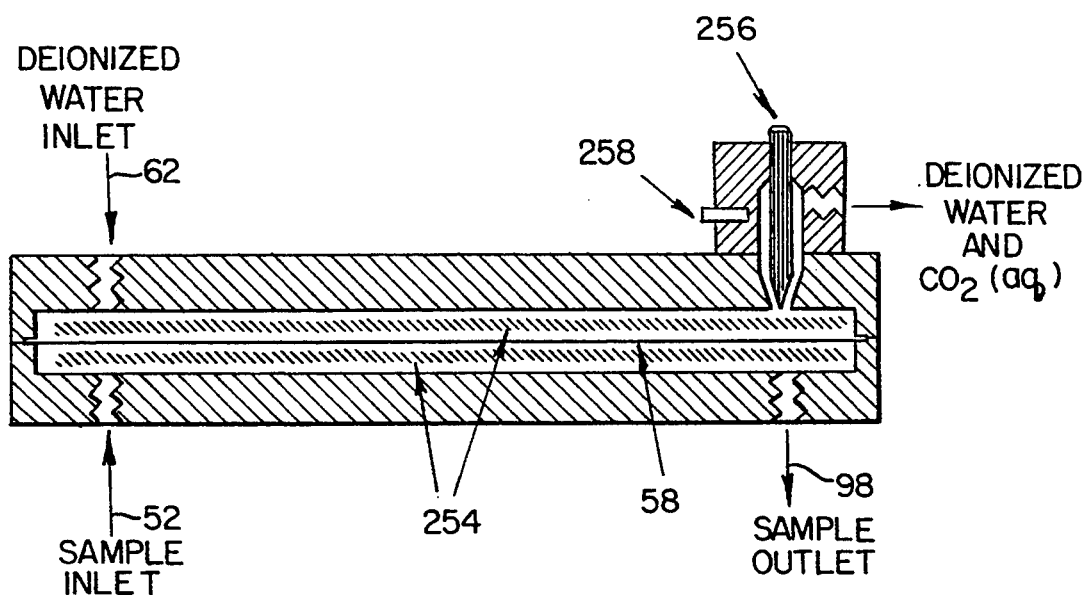
FIG. 12 is a schematic representation of the carbon dioxide sensor component of the present invention with an internal conductivity sensor.

A second embodiment of the carbon dioxide sensor is shown in FIG. 12. In this design, conduit 92 has been eliminated and the conductivity electrode 256 and temperature sensor 258 are an integral part of the carbon dioxide sensor.

Figure 13:
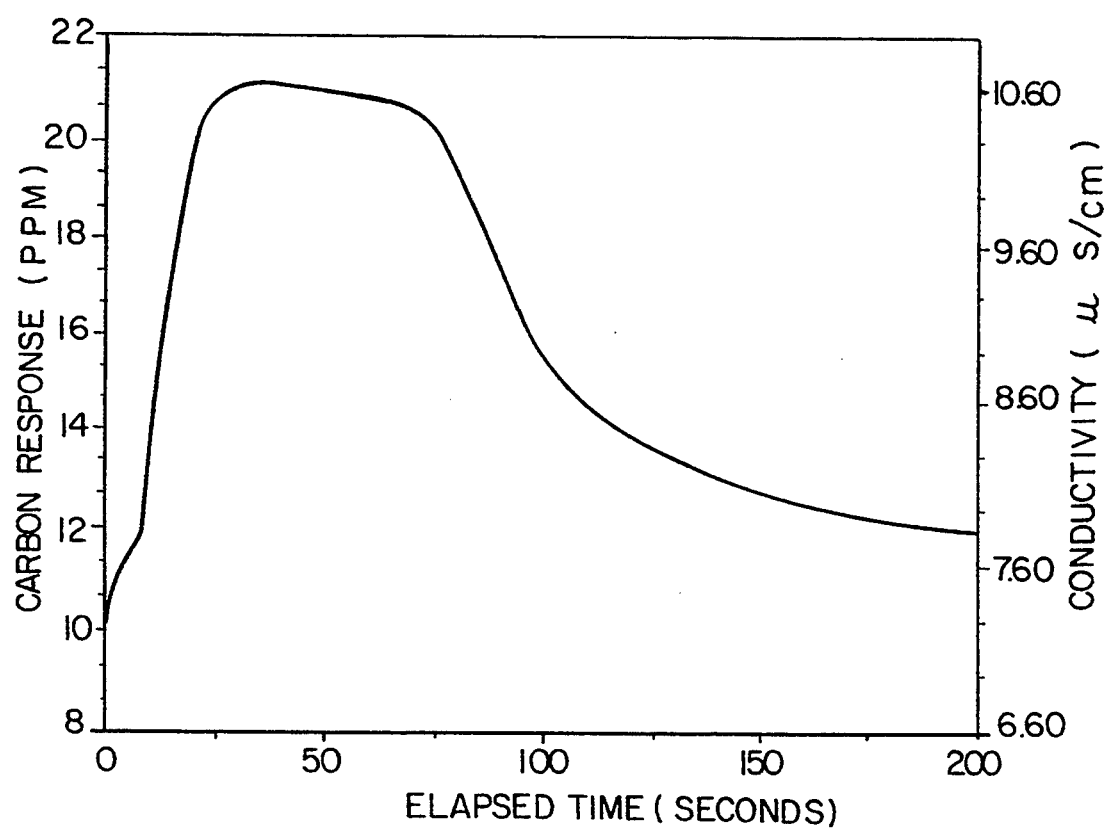
FIG. 13 is a representation of the output from the conductivity sensor during a measurement cycle.
Figure 14:
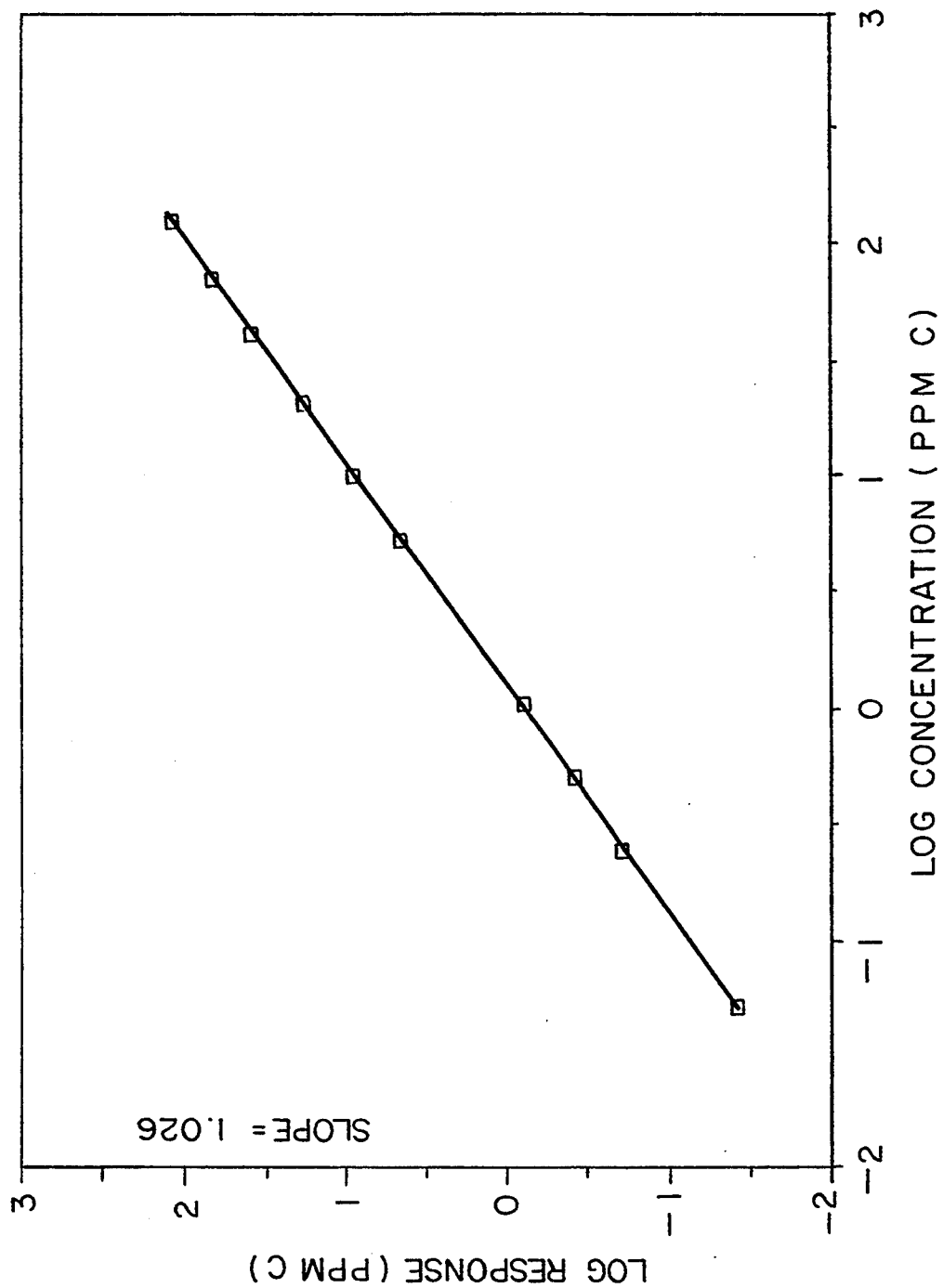
FIG. 14 is a plot of the logarithm of the response of the conductivity sensor versus the logarithm of the concentration of carbon in the aqueous sample.

Representative examples of the performance characteristics of the carbon dioxide sensor described in FIG. 11 are shown in FIG. 13 and FIG. 14 and in Table 1. As described above, the operation of the sensor 56 is based on the establishment of an equilibrium across a carbon dioxide selective gas permeable membrane existing between the aqueous sample stream and a deionized water sample. After this equilibrium has been established (typically 5 minutes), the deionized water sample containing carbon dioxide in the form of carbonate and bicarbonate water is swept into the microconductivity sensor by the introduction of a pulse of deionized water from the deionized water module. A plot of the response of the micro-conductivity sensor versus time as the equilibrated water sample enters the conductivity detector is shown in FIG. 13. As shown the output of the conductivity sensor increases rapidly as the sample flows into the cell. After a short period of time (approximately 30 seconds), the conductivity reaches its maximum value and remains at about that value for approximately 50 seconds. At this point in the measurement cycle, the conductivity is recorded and used in the calculation of total organic carbon concentration or total carbon concentration.

The carbon dioxide sensor has a linear response to the concentration of carbon dioxide in the aqueous sample stream as shown in FIG. 14 for the analysis of aqueous samples containing 0.05 to 125 mg/L of carbon. This data is presented to demonstrate the linearity of the carbon dioxide sensor and does not represent the full range of organic and inorganic carbon concentrations that can be determined using the present invention.

The carbon dioxide membrane 58 employed in the carbon dioxide sensor in one embodiment of the present invention was constructed from a Teflon-like material, perfluoroalkoxy resin ("PFA"). As shown in Table I, the use of this material in the carbon dioxide sensor provides significantly higher selectivity for the passage of carbon dioxide compared with other compounds which may be present in aqueous samples and potentially interfere in the measurement of carbon dioxide using the

TABLE 1

Selectivity of permeable membranes: potential interferences in $CO_2$ measurements

| COMPOUND | SPIKE CONCENTRATION | DETECTOR RESPONSE (ppm C) | | |
|---|---|---|---|---|
| | | PFA | POROUS* PTFE | Tefzel* |
| $I_2$ | 13 ppm | ND | — | — |
| $HNO_3$ | 1000 ppm | ND | — | — |
| $Na_2SO_4$ | 1000 ppm | ND | — | — |
| $Na_2SO_3$ | 21 ppm | ND | 1 | 0.4 |

TABLE 1-continued

Selectivity of permeable membranes:
potential interferences in $CO_2$ measurements

| COMPOUND | SPIKE CON-CENTRATION | DETECTOR RESPONSE (ppm C) | | |
|---|---|---|---|---|
| | | PFA | POROUS* PTFE | Tefzel* |
| $NaNO_2$ | 11 ppm | 0.2 | 5 | 0.6 |
| NaCl | 1000 ppm | ND | — | — |
| NaOCl | 10 ppm | ND | — | — |
| $Na_2S$ | 15 ppm | 0.05 | 6 | 0.4 |
| $Na_2S$ | 150 ppm | 2.0 | 30 | 2.0 |
| Formic Acid | 10 ppm | ND | 1 | 0.7 |
| Acetic Acid | 10 ppm | ND | 1 | 0.6 |

*From Kobos, et al.
ND: no detectable increase
—: data not reported conductometric technique described in the invention. For comparison purposes, data reported by Kobos et al. in 54 Anal. Chem. 1976–1980 (1982) are included in Table I.

Figure 15:
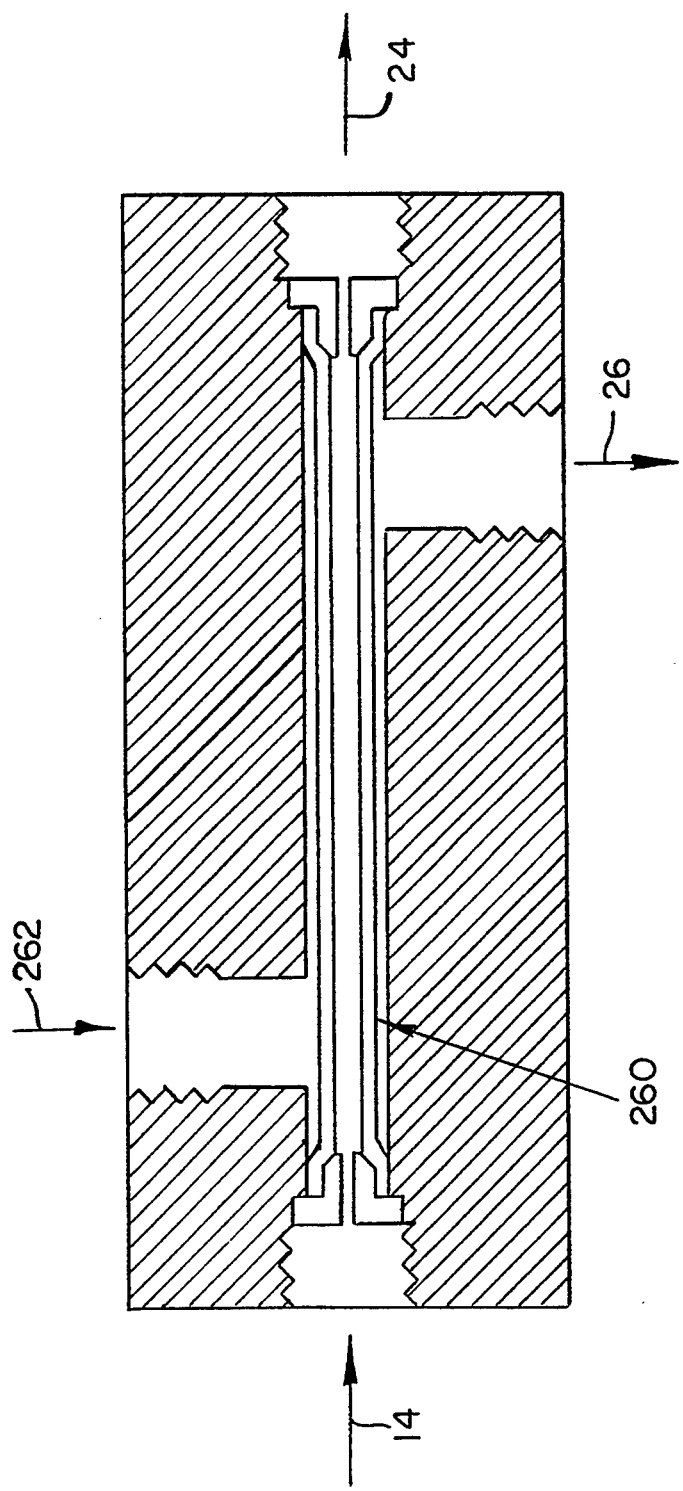
FIG. 15 is a schematic of the acidification module component of the present invention.

A more detailed description of the acidification module 16 is shown in FIG. 15. The filter outlet conduit is used to transport the aqueous sample into the interior of a hollow membrane 260. Aqueous acid from either the acid reservoir 18 or the acid/base generation module 110 passes through the acid inlet conduit 262, which is the equivalent of conduit 20 in FIG. 1 or conduit 112 in FIG. 2. The housing for the acidification module is constructed from polyvinylidene difluoride "PVDF" plastic to minimize possible contamination of the aqueous sample.

In summary, the different embodiments of the present invention described above represent significant improvements over the methods and apparatus existing for the measurement of total organic carbon and total carbon content of aqueous samples. The present invention can be used for these determinations in a wide range of samples, with minimal use of external chemical reagents. As outlined below, each of the individual components of the present invention also offer significant improvements over the prior art.

The use of a carbon dioxide selective membrane and conductometric detection applied to the measurement of total organic carbon and total inorganic carbon concentrations in aqueous samples offers these specific advantages: 1) no purge gas, gas/liquid purge apparatus or drying system is required, 2) the conductrometric detection system provides excellent long-term calibration stability and minimal fouling or contamination since the sensor is only exposed to carbon dioxide in deionized water, 3) the size of the conductivity sensor can be sufficiently small that accurate measurement in samples as small as 0.1 mL can be achieved, even at the instrument detection limit, 4) conductrometric detection provides a large linear dynamic range, typically one to three orders of magnitude greater than other techniques utilized for the measurement of carbon dioxide in aqueous samples, 5) the sensitivity of the carbon dioxide sensor and conductivity detector is substantially lower than other techniques (detection limits approximately 2–5 ug/L of carbon), 6) no sample clean-up or dilution is required, 7) the combination of an inorganic carbon removal module and a carbon dioxide sensor virtually eliminates any interference from other volatile gases, and 8) the detector response is insensitive to changes in sample flow rate.

The U.V. oxidation module of the present invention incorporates several new techniques which offer distinct advantages over existing techniques for the oxidation of organic compounds to form carbon dioxide. The use of an n-type semiconductor as a catalyst to photooxidize organic compounds for the measurement of organic compounds in water is novel, in that no external chemical oxidizing reagents are required for samples containing up to 10 mg/L of carbon. With the addition of oxygen (either generated photolytically or electrochemically) efficient oxidation can be achieved for samples containing as high as 30 mg/L of carbon. The in-situ generation of persulfate ion permits the present invention to measure total organic compounds in concentrations as high as 1000 mg/L.

The use of aqueous solution of persulfate is widely used for the oxidation of organic compounds in the determination of total organic carbon in water. However, this reagent is unstable and fresh solution must be prepared, typically once a month. The in-situ generation of persulfate using the electrolysis of aqueous sulfate solutions overcomes this problem. In addition, the electrolysis of aqueous sulfate solutions also results in the generation of hydrogen peroxide which is a powerful oxidizing agent.

Electrolytic generation of oxygen in aqueous solution for the determination of total organic carbon is disclosed by Winkler. However, the present invention improves upon the disclosure of Winkler in two key areas. First we have effected a simplification of the electrolysis system. Winkler teaches the use of a solid polymer electrolyte positioned between the anode and the cathode. In the present invention, no solid polymer electrolyte is required and the cathode is constructed from palladium, which is selectively permeable to molecular hydrogen. This improved design permits the generation of an oxidizing agent at the anode and the instantaneous absorption, diffusion and expulsion of hydrogen generated at the cathode.

As previously noted, photo-decomposition of the solid polymer electrolyte will occur in Winkler's device, leading to a background source of carbon in the system. The simplification of the electrolysis module by elimination of the solid polymer electrolyte eliminates this background contamination. Another problem inherent in the Winkler design is that the aqueous sample will permeate into the solid polymer electrolyte. Organic compounds or carbon dioxide dissolved in this entrained water will eventually diffuse back into the bulk sample causing at least an increased analysis time, and at worst, cross-contamination between samples resulting in erroneous measurements.

We claim:
1. A process for the measurement of carbon compounds, comprising: acidifying an aqueous sample in a sample stream containing carbon dioxide, bicarbonate, carbonate and organic carbon, to convert bicarbonate and carbonate into carbon dioxide; removing the carbon dioxide from said sample stream in an inorganic carbon removal module;
   converting organic carbon in said sample stream into carbon dioxide in an oxidation reactor; and
   passing the sample stream containing carbon dioxide into carbon dioxide detection means including a carbon dioxide permeable membrane with two sides, having the sample stream on one side and deionized water on the other side, whereby carbon dioxide passes through the membrane from the sample stream to the deionized water to form water with carbon dioxide in solution; and measuring the conductivity and temperature of the dioxide concentration in the water with carbon dioxide in solution.

2. The process of claim 1 wherein the inorganic carbon removal module includes a gas permeable membrane through which the carbon dioxide passes.

3. The process of claim 1 wherein the oxidation reactor includes a photo-reactor having:
a source of ultra-violet radiation; and an ultra-violet radiation transparent sample chamber, said sample chamber having a sample stream inlet and outlet.

4. The process of claim 1 wherein the oxidation reactor includes:
an in-line electrolysis cell for the generation of oxidizing agents from the electrolysis of water; and
a photo-reactor having: a source of ultraviolet radiation; and an ultra-violet radiation transparent sample chamber, said sample chamber having a sample stream inlet and outlet.

5. The process of claim 1 wherein the oxidation reactor includes:
means for introducing an aqueous solution containing an oxidizing agent into the sample stream; and
a photo-reactor having: a source of ultraviolet radiation; an ultra-violet radiation transparent sample chamber, said sample chamber having a sample stream inlet and outlet.

6. The process of claim 1 wherein the oxidation reactor includes a combined electrolysis/photolysis oxidation system for the generation of oxidizing agents and electrochemical and photochemical oxidation of organic compounds, and further includes:
a) a sample chamber constructed from an ultra-violet radiation transparent material to permit exposure of the sample stream to ultra-violet radiation;
b) an ultra-violet radiation source in radiative communication with said sample stream;
c) electrolytic cell means disposed in said sample chamber comprising an anode adjacent to said sample stream, said anode in electrical communication with said sample stream, a cathode adjacent to and in electrical contact with said sample stream, said cathode being substantially impermeable to water and permeable to hydrogen;
d) means for receiving generated hydrogen adjacent to said cathode; and
e) means for removing hydrogen from said receiving means.

7. A process for the measurement of carbon compounds, comprising:
acidifying an aqueous sample in a sample stream containing carbon dioxide, bicarbonate, carbonate and organic carbon, to convert bicarbonate and carbonate into carbon dioxide;
converting organic carbon in said sample stream into carbon dioxide in an oxidation reactor wherein the oxidation reactor includes sections of fused silica tubing connected to lengths of palladium tubing and a source of ultra-violet radiation, wherein said palladium tubing removes molecular hydrogen; and
passing the sample stream containing carbon dioxide into carbon dioxide detection means including a carbon dioxide permeable membrane with two sides, having the sample stream on one side and deionized water on the other side, whereby carbon dioxide passes through the membrane from the sample stream to the deionized water to form water with carbon dioxide in solution; and measuring the conductivity and temperature of the water with carbon dioxide in solution to determine the carbon dioxide concentration in the water with carbon dioxide in solution.

8. A process for the measurement of carbon compounds, comprising acidifying an aqueous sample in a sample stream containing carbon dioxide, bicarbonate, carbonate and organic carbon, to convert bicarbonate and carbonate into carbon dioxide;
converting organic carbon in said sample stream into carbon dioxide in an oxidation reactor wherein the oxidation reactor includes: means for adding sulfate ions to the sample stream; an in-line electrolysis cell for the generation of peroxydisulfate and other oxidizing agents by electrolysis; and a photo-reactor having: a source of ultraviolet radiation; and an ultra-violet radiation transparent sample chamber, said sample chamber having a sample stream inlet and outlet; and
passing the sample stream containing carbon dioxide into carbon dioxide detection means including a carbon dioxide permeable membrane with two sides, having the sample stream on one side and deionized water on the other side, whereby carbon dioxide passes through the membrane from the sample stream to the deionized water to form water with carbon dioxide in solution; and measuring the conductivity and temperature of the water with carbon dioxide in solution to determine the carbon dioxide concentration in the water with-carbon dioxide in solution.

9. A process for the measurement of carbon compounds comprising acidifying an aqueous sample in a sample stream containing carbon dioxide, bicarbonate, carbonate and organic carbon, to convert bicarbonate and carbonate into carbon dioxide;
converting organic carbon in said sample stream into carbon dioxide in an oxidation reactor wherein the oxidation reactor includes means for introduction peroxydisulfate to the sample stream; and a photo-reactor having: a source of ultraviolet radiation; and an ultra-violet radiation transparent sample chamber, said sample chamber having a sample stream inlet and outlet; and
passing the sample stream containing carbon dioxide into carbon dioxide detection means including a carbon dioxide permeable membrane with two sides, having the sample stream on one side and deionized water on the other side, whereby carbon dioxide passes through the membrane from the sample stream to the deionized water to form water with carbon dioxide in solution; and measuring the conductivity and temperature of the water with carbon dioxide in solution to determine the carbon dioxide concentration in the water with carbon dioxide in solution.

10. A process for the measurement of the total organic carbon, total inorganic carbon and total carbon content of aqueous samples comprising:
(a) acidifying a sample stream containing an aqueous sample in an acidification module to convert bicarbonate and carbonate in the aqueous sample into carbon dioxide;
(b) dividing said stream in a stream splitting device into first and second streams;
(c) passing said second sample stream containing carbon dioxide formed in the acidification module into a carbon dioxide detector having a gas permeable membrane selective for the passage of carbon dioxide separating the sample stream from a deionized water stream; wherein carbon dioxide is diffused across the membrane into the deionized water to form water with carbon dioxide in solution, and said water with carbon dioxide in solution is passed into a conductivity and temperature measurement cell for measurement of the total concentration of ionic species in, and the temperature of, the water with carbon dioxide in solution, said concentration of ionic species being proportional to the concentration of inorganic carbon present in the aqueous sample;

(d) passing said first sample stream into an oxidation reactor for the conversion of organic compounds to carbon dioxide; said first sample stream from the oxidation reactor passing into a carbon dioxide detector having a gas permeable membrane selective for the passage of carbon dioxide separating the sample stream from a deionized water stream wherein carbon dioxide is diffused across the membrane into the deionized water with carbon dioxide in solution; and said water with carbon dioxide in solution is passed into a conductivity and temperature measurement cell for measurement of the total concentration of ionic species in, and the temperature of, the water with carbon dioxide in solution, said concentration of ionic species being proportional to the concentration of the total carbon species in the aqueous sample; and (e) calculating the concentration of total organic carbon present in the aqueous sample from the difference in measured total carbon species concentration and total inorganic carbon species concentration.

11. A process for the measurement of the total organic carbon, total inorganic carbon and total carbon content comprising:

(a) acidifying a sample stream containing an aqueous sample in an acidification module to convert bicarbonate and carbonate species in the aqueous sample into carbon dioxide;

(b) introducing said sample stream into an oxidation reactor having control means for either permitting complete oxidation of organic compound in the sample stream to form carbon dioxide or preventing oxidation of any organic compounds;

(c) controlling said oxidation reactor to prevent oxidation of the organic compounds in the sample stream at a first time and passing the sample stream into an apparatus containing a gas permeable membrane selective for the passage of carbon dioxide separating the sample stream from a deionized water stream, allowing diffusion of the carbon dioxide from this sample stream across the membrane into the deionized water to form water with carbon dioxide in solution, and passing said water with carbon dioxide in solution into a conductivity and temperature measurement cell for measurement of the total concentration of ionic species in, and the temperature of, the water with carbon dioxide in solution, the concentration of ionic species being proportional to the concentration of inorganic carbon species present in the aqueous sample;

(d) controlling said oxidation reactor such that complete oxidation of organic compounds occurs in the sample stream at a second time different than the first time, and passing the sample stream containing carbon dioxide into an apparatus containing a gas permeable membrane selective for the passage of carbon dioxide separating the sample stream from a deionized water stream; allowing diffusion of the carbon dioxide from the sample stream across the membrane into the deionized water to form water with carbon dioxide in solution, and passing said water with carbon dioxide in solution into a conductivity and temperature measurement cell for measurement of the total concentration of ionic species in, and temperature of, the water with carbon dioxide in solution, the concentration of ionic species being proportional to the concentration of the total carbon species in the aqueous sample; and (e) calculating the concentration of total organic carbon species present in the aqueous sample from the difference in measured total carbon species concentration and total inorganic carbon species concentration.

* * * * *

UNITED STATES PATENT AND TRADEMARK OFFICE
CERTIFICATE OF CORRECTION

PATENT NO. : 5,443,991
DATED : August 22, 1995
INVENTOR(S) : Richard D. Godec, Paul K. Losenka, and Richard Hutte It is certified that error appears in the above-indentified patent and that said Letters Patent is hereby corrected as shown below:

Column 21, lines 1 and 2, change "conductivity and temperature of the dioxide concentration in the water with carbon dioxide in solution."

to "conductivity and temperature of the water with carbon dioxide in solution to determine the carbon dioxide concentration in the water with carbon dioxide in solution."

Signed and Sealed this

Nineteenth Day of December, 1995

Attest:

BRUCE LEHMAN

*Attesting Officer*     *Commissioner of Patents and Trademarks*